US008821583B2

(12) United States Patent
Myung et al.

(10) Patent No.: US 8,821,583 B2
(45) Date of Patent: *Sep. 2, 2014

(54) INTERPENETRATING POLYMER NETWORK HYDROGEL

(75) Inventors: David Myung, Santa Clara, CA (US); Laura Hartmann, San Francisco, CA (US); Jean Noolandi, Palo Alto, CA (US); Christopher N. Ta, Saratoga, CA (US); Curtis W. Frank, Cupertino, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 733 days.

This patent is subject to a terminal disclaimer.

(21) Appl. No.: 12/070,336

(22) Filed: Feb. 15, 2008

(65) Prior Publication Data
US 2008/0269370 A1    Oct. 30, 2008

Related U.S. Application Data

(63) Continuation-in-part of application No. 11/243,952, filed on Oct. 4, 2005, now Pat. No. 7,857,849, and a
(Continued)

(51) Int. Cl.
*A61F 2/08* (2006.01)
*A61L 27/52* (2006.01)
*A61L 27/38* (2006.01)

(52) U.S. Cl.
CPC ...... *A61L 27/52* (2013.01); *A61L 27/38* (2013.01)
USPC ........ 623/23.58; 424/423; 424/487; 523/114; 524/377; 516/98

(58) Field of Classification Search
CPC ................................. C08L 2204/04
USPC ...................... 523/105, 113; 623/23.58, 23.6; 424/484, 486
See application file for complete search history.

(56) References Cited

U.S. PATENT DOCUMENTS 4,973,493 A * 11/1990 Guire ............................ 427/2.24
5,580,929 A   12/1996 Tanaka
(Continued)

FOREIGN PATENT DOCUMENTS

| WO | WO 00/02937     | * | 1/2000 |
| WO | WO 03/093337    | * | 4/2003 |
| WO | WO 2005/056608  |   | 6/2005 |

OTHER PUBLICATIONS

Myung et al. Polymer 48 (2007) pp. 5376-5387.*
(Continued)

*Primary Examiner* — Michael Pepitone
*Assistant Examiner* — Michael A Salvitti
(74) *Attorney, Agent, or Firm* — Lumen Patent Firm

(57) ABSTRACT

A strain-hardened interpenetrating polymer network (IPN) hydrogel is provided. The interpenetrating polymer network hydrogel is based on two different networks. The first network is a non-silicone network of preformed hydrophilic non-ionic telechelic macromonomers chemically cross-linked by polymerization of its end-groups. The second network is a non-silicone network of ionizable monomers. The second network has been polymerized and chemically cross-linked in the presence of the first network and has formed physical cross-links with the first network. An aqueous salt solution having a neutral pH is used to ionize and swell the second network in the interpenetrating polymer network. The swelling of the second network is constrained by the first network, and this constraining effect results in an increase in effective physical cross-links within the interpenetrating polymer network, and, in turn, an increase its elastic modulus. The strain-hardened interpenetrating polymer network hydrogel is attractive and useful for medical, industrial, and personal hygiene purposes.

15 Claims, 23 Drawing Sheets

Related U.S. Application Data continuation-in-part of application No. 11/636,114, filed on Dec. 7, 2006, now Pat. No. 7,857,447, and a continuation-in-part of application No. 11/409,218, filed on Apr. 20, 2006, now abandoned, and a continuation-in-part of application No. 11/639,049, filed on Dec. 13, 2006, now Pat. No. 7,909,867.

(60) Provisional application No. 60/901,805, filed on Feb. 16, 2007, provisional application No. 60/616,262, filed on Oct. 5, 2004, provisional application No. 60/673,172, filed on Apr. 20, 2005, provisional application No. 60/843,942, filed on Sep. 11, 2006, provisional application No. 60/783,307, filed on Mar. 17, 2006, provisional application No. 60/673,600, filed on Apr. 21, 2005.

(56) References Cited

U.S. PATENT DOCUMENTS

| | | | |
|---|---|---|---|
| 5,976,648 | A | 11/1999 | Li |
| 6,005,160 | A | 12/1999 | Hsiue |
| 6,224,893 | B1 | 5/2001 | Langer et al. |
| 6,372,815 | B1 | 4/2002 | Sulc |
| 6,638,991 | B2 | 10/2003 | Baba et al. |
| 7,279,507 | B2 * | 10/2007 | Hu et al. ............ 523/108 |
| 2003/0083389 | A1 | 5/2003 | Kao |
| 2003/0220245 | A1 | 11/2003 | Hubbell et al. |
| 2005/0090612 | A1 * | 4/2005 | Soane et al. ............ 524/800 |
| 2005/0147685 | A1 * | 7/2005 | Osada et al. ............ 424/487 |
| 2006/0083773 | A1 * | 4/2006 | Myung et al. ............ 424/427 |
| 2006/0188940 | A1 | 8/2006 | Cima et al. |
| 2007/0126982 | A1 | 6/2007 | Myung et al. |
| 2007/0179605 | A1 | 8/2007 | Myung |
| 2009/0088846 | A1 * | 4/2009 | Myung et al. ............ 623/14.12 |

OTHER PUBLICATIONS

Kim et al. Reactive & Functional Polymers 55 (2003) pp. 69-73.*
Kim et al. Journal of Applied Polymer Science vol. 89, pp. 2301-2305 (2003).*
pH (Titration) curves. pp. 1-11. Obtained from http://www.chemguide.co.uk/physical/acidbaseeqia/phcurves.html. No Author, No Date. Obtained on Jun. 5, 2012.*
Gong et al. Double-Network Hydrogels with Extremely High Mechanical Strength. Adv. Materials 15 (14) 1155-1158, 2003.
Hern et al. Incorporation of adhesion peptides into nonadhesive hydrogels useful for tissue resurfacing. J. Biomed. Materials Research 39(1) 266-276, 1998.
Evans et al. The use of corneal organ culture in biocompatibility studies. Biomaterials 23 1359-1367, 2002.
"Structure, Properties, and Medical Device Applications of Mechanically Enhanced, Biometric Hydrogel Alloys." David Myung. Doctoral Thesis. Stanford University. Dec. 2007. www.proquest.umi.com.ezacess.libraries.psu.edu/pqdweb?index.
Presentation at American Chemical Society Meeting, Sep. 11, 2006, "Biometric Hydrogels." Curtis Frank. San Francisco, CA. From http://new-service.stanford.edu/new/september13/cornea-091306.html.
Elbert at al. (2001) Conjugate addition reactions combined with free-radical cross-linking for the design of materials for tissue engineering. Biomacromolecules. 2001 2(2):430-41.

* cited by examiner

A                              B

INTERPENETRATING POLYMER NETWORK HYDROGEL

CROSS-REFERENCE TO RELATED APPLICATIONS

This application claims priority from U.S. Provisional Application No. 60/901,805, filed on Feb. 16, 2007, which is incorporated herein by reference. This application is a continuation-in part of U.S. patent application Ser. No. 11/243, 952, filed Oct. 4, 2005, now U.S. Pat. No. 7,857,849 which is incorporated herein by reference. U.S. patent application Ser. No. 11/243,952, filed Oct. 4, 2005 claims the benefit of U.S. Provisional Applications 60/616,262 filed on Oct. 5, 2004 and 60/673,172 filed on Apr. 20, 2005. This application is also a continuation-in-part of U.S. application Ser. No. 11/636,114, filed Dec. 7, 2006, now U.S. Pat. No. 7,857,447 which is incorporated herein by reference. U.S. application Ser. No. 11/636,114, filed Dec. 7, 2006 claims the benefit of U.S. Provisional Application No. 60/843,942, filed on Sep. 11, 2006, and 60/783,307, filed Mar. 17, 2006. This application is further a continuation-in-part of U.S. application Ser. No. 11/409,218, filed Apr. 20, 2006, now abandoned which is incorporated herein by reference. U.S. application Ser. No. 11/409,218, filed Apr. 20, 2006 claims the benefit of U.S. Provisional Application No. 60/673,600, filed Apr. 21, 2005. This application is further a continuation-in-part of U.S. application Ser. No. 11/639,049, filed Dec. 13, 2006, now U.S. Pat. No. 7,909,867 which is incorporated herein by reference. U.S. application Ser. No. 11/639,049, filed Dec. 13, 2006 claims the benefit of U.S. Provisional Application No. 60/843,942, filed on Sep. 11, 2006.

FIELD OF THE INVENTION

The present invention relates generally to interpenetrating polymer network hydrogels. More particularly, the present invention relates to materials useful for medical, industrial, and personal hygiene purposes including but not limited to orthopedic prostheses, ophthalmic implants and lenses, artificial tissues and organs, cell scaffolds, transplantation vehicles, absorbent diapers, feminine hygiene products, biosensors, surface coatings, shock-absorbing materials, and lubricating materials.

BACKGROUND OF THE INVENTION

Hydrogels are water-swollen polymers that are useful in a variety of biomedical device applications due to their biocompatibility, high water content, and in some cases, responsiveness to stimuli. Unfortunately, the mechanical fragility of most hydrogels poses a formidable obstacle to their application in many applications, which require a high elastic modulus and high mechanical strength. Although a number of strategies—such as high crosslinking density, fiber-reinforcement, and copolymerization—can be used to improve the strength of hydrogels, the enhancement afforded by these often involves some compromise in the desired characteristics of the original material, such as hydrophilicity, transparency, or permeability. For many tissue replacement applications, maintenance of these properties is critical to their performance/in vivo/. Accordingly, there is a need in the art to develop hydrogels with high values for Young's modulus and tensile strength that would at least overcome some of these disadvantages. The present invention addresses these needs and provides a strain-hardened interpenetrating polymer network hydrogel with high elastic modulus and a method for fabricating this material.

SUMMARY OF THE INVENTION

The present invention provides a strain-hardened interpenetrating polymer network (IPN) hydrogel. The interpenetrating polymer network hydrogel is based on two different networks. The first network is a non-silicone network of preformed hydrophilic non-ionic telechelic macromonomers chemically cross-linked by polymerization of its end-groups. The second network is a non-silicone network of ionizable monomers. The second network has been polymerized and chemically cross-linked in the presence of the first network and has formed physical cross-links with the first network. Within the interpenetrating polymer network, the degree of chemical cross-linking in the second network is less than the degree of chemical cross-linking in the first network. An aqueous salt solution having a neutral pH is used to ionize and swell the second network in the interpenetrating polymer network. The swelling of the second network is constrained by the first network, and this constraining effect results in an increase in effective physical cross-links within the interpenetrating polymer network. The strain-induced increase in physical cross-links is manifested as a strain-hardened interpenetrating polymer network with an increased initial Young's modulus, which is larger than the initial Young's modulus of either (i) the first network of hydrophilic non-ionic telechelic macromonomers swollen in pure water or in an aqueous salt solution, (ii) the second network of ionized monomers swollen in pure water or in an aqueous salt solution, or (iii) the interpenetrating polymer network hydrogel formed by the combination of the first and second network swollen in pure water. The observed increase in Young's modulus as a result of strain (induced herein by swelling) is caused by an increase in the number of physical cross-links within the interpenetrating polymer network. For the purposes of the present invention, strain-hardening is defined as an increase in the number of physical cross-links and Young's modulus with applied strain.

The interpenetrating polymer network of the present invention could be varied according to the following embodiments either by themselves or in any combinations thereof. For example, the hydrophilic non-ionic macromonomer in the first network has a molecular weight between about 275 Da to about 20,000 Da, about 1000 Da to about 10,000 Da, or about 3000 Da to about 8000 Da. In another example, the molar ratio between the ionizable monomers and the hydrophilic non-ionic telechelic macromonomers is greater than or equal to 1:1 or greater than 100:1. In still another example, the aqueous salt solution has a pH in the range of about 6 to 8. In still other examples, the first network has at least about 50%, at least 75% or at least 95% by dry weight telechelic macromonomers. In still another example, the first network has hydrophilic monomers grafted onto the first network. In still another example, the second network further has hydrophilic macromonomers grafted onto the second polymer network. In still another example, the strain-hardened interpenetrating polymer network hydrogel has a tensile strength of at least about 1 MPa. In still another example, the strain-hardened interpenetrating polymer network hydrogel has an initial Young's modulus of at least about 1 MPa. In still another example, the strain-hardened interpenetrating polymer network hydrogel has an oxygen permeability of at least 15 Barrers. In still another example, the strain-hardened interpenetrating polymer network hydrogel has an equilibrium water content of at least 50%. In still another example, the strain-hardened interpenetrating polymer network hydrogel is at least about 70% transparent. In still another example, the coefficient of friction of the strain-hardened interpenetrating polymer network hydrogel in an aqueous solution is less than 0.2. In still another example, biomolecules are tethered to the surface of the strain-hardened interpenetrating polymer network hydrogel using azide-active-ester linkages. In one example, the biomolecules could be used to support cell adhesion.

At least some of the characteristics of the strain-hardened interpenetrating polymer network hydrogel make this new hydrogel advantageous over conventional hydrogels. Accordingly, the strain-hardened interpenetrating polymer network hydrogel is attractive and useful for medical, industrial, and personal hygiene purposes including but not limited to orthopedic implants, ophthalmic implants and lenses, contact lenses, artificial corneas, artificial cartilage, artificial tissues and organs, cell scaffolds, transplantation vehicles, absorbent diapers, feminine hygiene products, biosensors, surface coatings, shock-absorbing materials, and lubricating materials.

BRIEF DESCRIPTION OF THE FIGURES

The present invention together with its objectives and advantages will be understood by reading the following description in conjunction with the drawings, in which.

DETAILED DESCRIPTION

Figure 1:
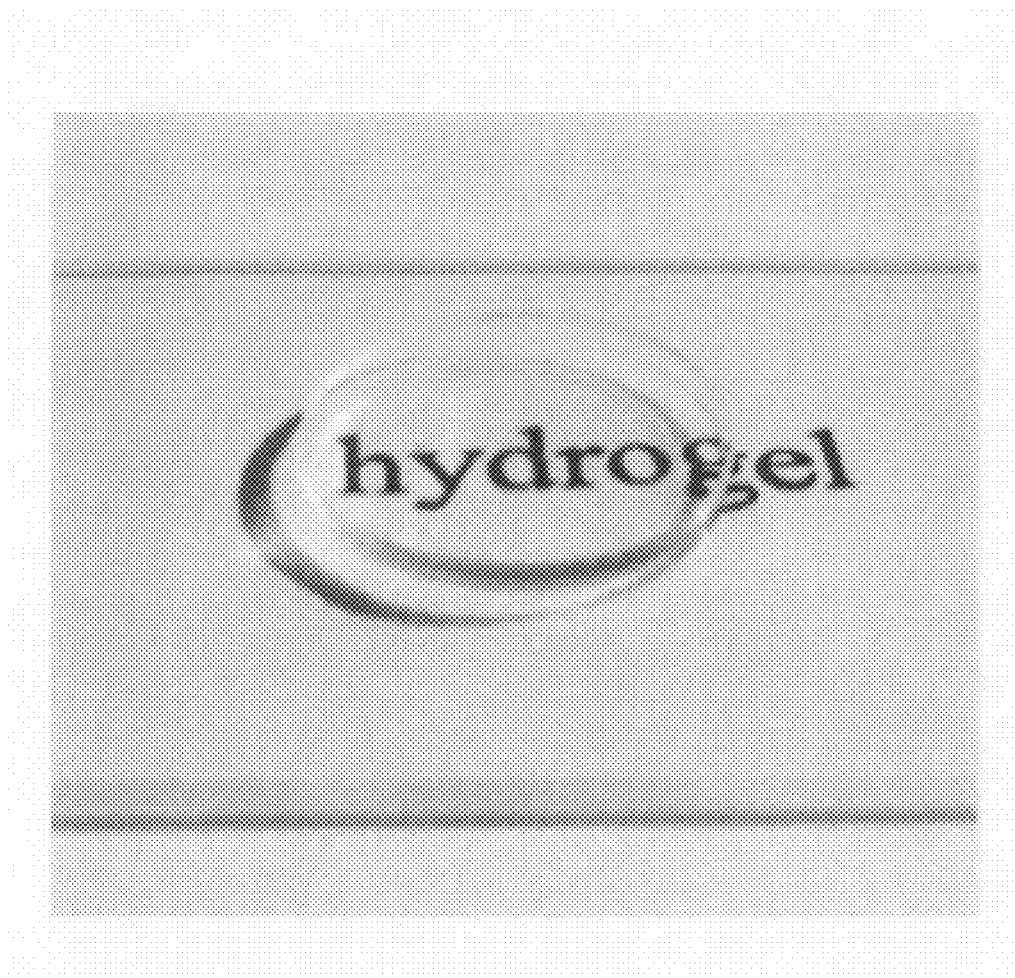
FIG. 1 shows according to an embodiment of the present invention a mechanically enhanced interpenetrating polymer network (IPN) hydrogel based on an end-linked first network and an ionized second network.

The present invention provides an interpenetrating polymer network (IPN) hydrogel network based on a neutral cross-linked network of end-linked macromonomers in the first network and an ionizable crosslinked polymer in the second network. In one of the embodiments, the first network is composed of end-linked poly(ethylene glycol) macromonomers with defined molecular weight. The second network is, in contrast, a loosely crosslinked, ionizable network of poly(acrylic acid) (PAA). A photograph of the swollen PEG/PAA hydrogel is shown in FIG. 1. This PEG/PAA IPN has high tensile strength, high compressive strength, and a low coefficient of friction when swollen in phosphate buffered saline at a pH of 7.4.

Homopolymer networks of PEG and PAA are both relatively fragile materials (the former is relatively brittle, the latter is highly elastic), so neither would be expected to make the sole contribution to mechanical strength enhancement. However, the two polymers can form complexes through hydrogen bonds between the ether groups on PEG and the carboxyl groups on PAA. This inter-polymer hydrogen bonding enhances their mutual miscibility in aqueous solution, which, in turn, yields optically clear, homogeneous polymer blends. By loosely cross-linking (instead of densely cross-linking) the ionizable network (PAA, $pK_a$=4.7), large changes in its network configuration can be induced by changing the pH of the solvent without affecting the neutral PEG network. At a pH greater than 4.7, the PAA network becomes charged and swells; at a pH lower than 4.7, the PAA network is protonated and contracts.

Figure 2:
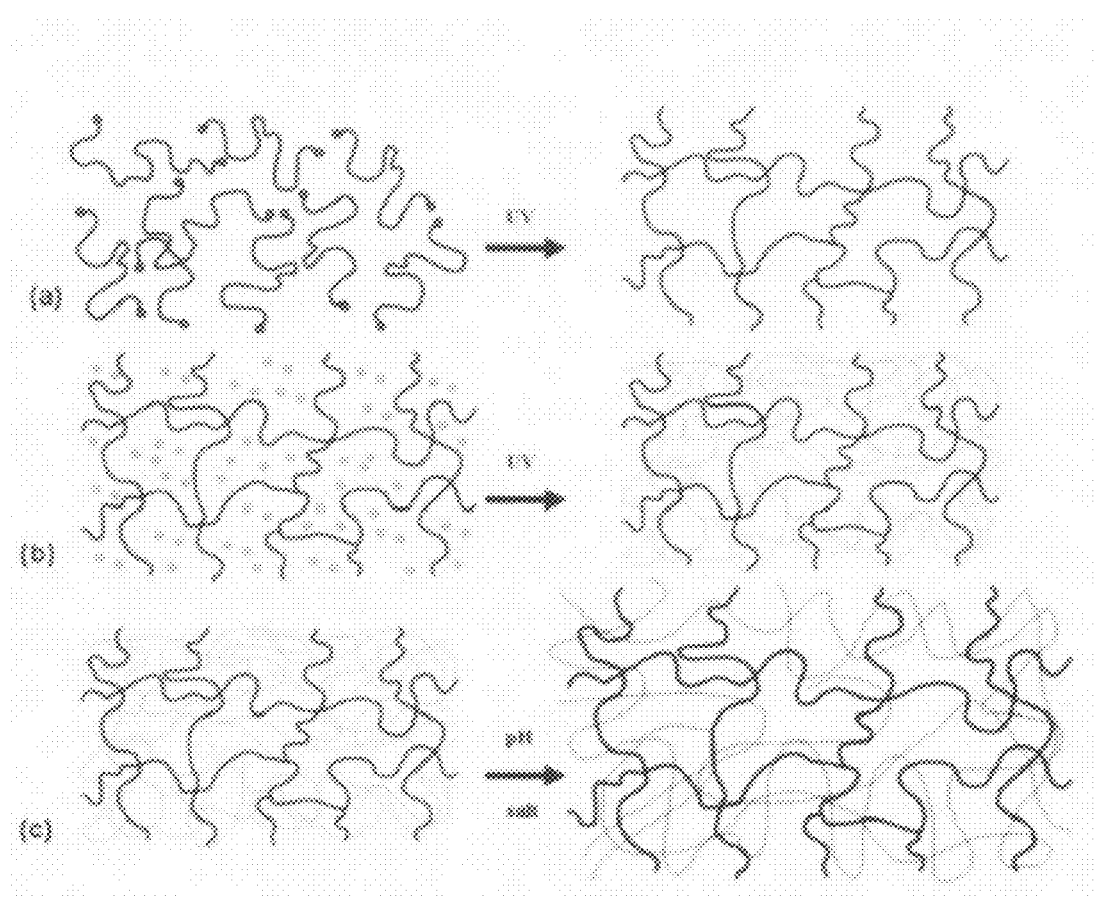
FIG. 2 shows the steps required for synthesis of an IPN hydrogel according to the present invention.
A. The starting material for the hydrogel is a solution of telechelic macromonomers (left) with functional end groups (circles) dissolved in water. The telechelic macromonomers are polymerized to form a first, water-swollen polymer network (right).
B. hydrophilic, ionizable monomers (stars) mixed with water are added to the first polymer network (left) along with a photoinitiator and a crosslinking agent. The hydrophilic, ionizable monomers are then photopolymerized and cross-linked in the presence of first polymer network to form second polymer network in the presence of the first. This results in formation of a water-swollen IPN hydrogel (FIG. 2B, right).
C. The water-imbibed IPN is then immersed in a salt-containing solution at a typical pH of 7.4 and is swollen to equilibrium, yielding an unusual simultaneous increase in both the water content and Young's modulus of the IPN. Despite having higher water content, the IPN on the right has a higher modulus compared to the IPN on the left due strain hardening induced by swelling of the second network within constraint posed by the highly crosslinked first network.

FIG. 2A shows the steps required for synthesis of an IPN hydrogel according to the present invention. The starting material for the hydrogel is a solution of telechelic macromonomers (left) with functional end groups (circles) dissolved in water (not shown). The telechelic macromonomers are polymerized to form a first, water-swollen polymer network (right). Next, (FIG. 2B) hydrophilic, ionizable monomers (stars) mixed with water are added to the first polymer network (left) along with a photoinitiator and a crosslinking agent. The hydrophilic, ionizable monomers are then photopolymerized and cross-linked in the presence of first polymer network to form second polymer network in the presence of the first. This results in formation of a water-swollen IPN hydrogel (FIG. 2B, right). The water-imbibed IPN is then immersed in a salt-containing solution at pH 7.4 (FIG. 2C), and is swollen to equilibrium, yielding an unusual simultaneous increase in both the water content and Young's modulus of the IPN. Despite having higher water content, the IPN on the right in FIG. 2C has a higher Young's modulus compared to the IPN on the left. This increase in modulus as a result of strain (induced in this case by swelling) is caused by an increase in the number of physical crosslinks within the IPN. For the purpose of the present invention, strain hardening is defined as an increase in physical crosslinks and Young's modulus with applied strain. When the IPN is strain-hardened, it is effectively "pre-stressed" in the sense that stress is built into the IPN network, yielding a material with an increased Young's modulus relative to its unstrained state.

Any hydrophilic telechelic macromonomer may be used to form the first polymer network. In a preferred embodiment, preformed polyethylene glycol (PEG) macromonomers are used as the basis of the first network. PEG is biocompatible, soluble in aqueous solution, and can be synthesized to give a wide range of molecular weights and chemical structures. The hydroxyl end-groups of the bifunctional glycol can be modified into crosslinkable end-groups. End-group or side-group functionalities to these macromolecules and biomacromolecules may include, but are not limited to, acrylate (e.g. PEG-diacrylate), methacrylate, vinyl, allyl, N-vinyl sulfones, methacrylamide (e.g. PEG-dimethacrylamide), and acrylamide (e.g. PEG-diacrylamide). For instance, PEG macromonomers can be chemically modified with endgroups such as diacrylates, dimethacrylates, diallyl ethers, divinyls, diacrylamides, and dimethacrylamides. These endgroups can be added to other macromonomers, such as polycarbonate, poly(N-vinyl pyrrolidone), polyurethane, poly(vinyl alcohol), polysacchrarides (e.g. dextran), biomacromolecules (e.g. collagen) and derivatives or combinations thereof. The first network can also be copolymerized with any number of other polymers including but not limited to those based on acrylamide, hydroxyethyl acrylamide, N-isopropylacrylamide, polyurethane, 2-hydroxyethyl methacrylate, polycarbonate, 2-hydroxyethyl acrylate or derivatives thereof.

Figure 3:
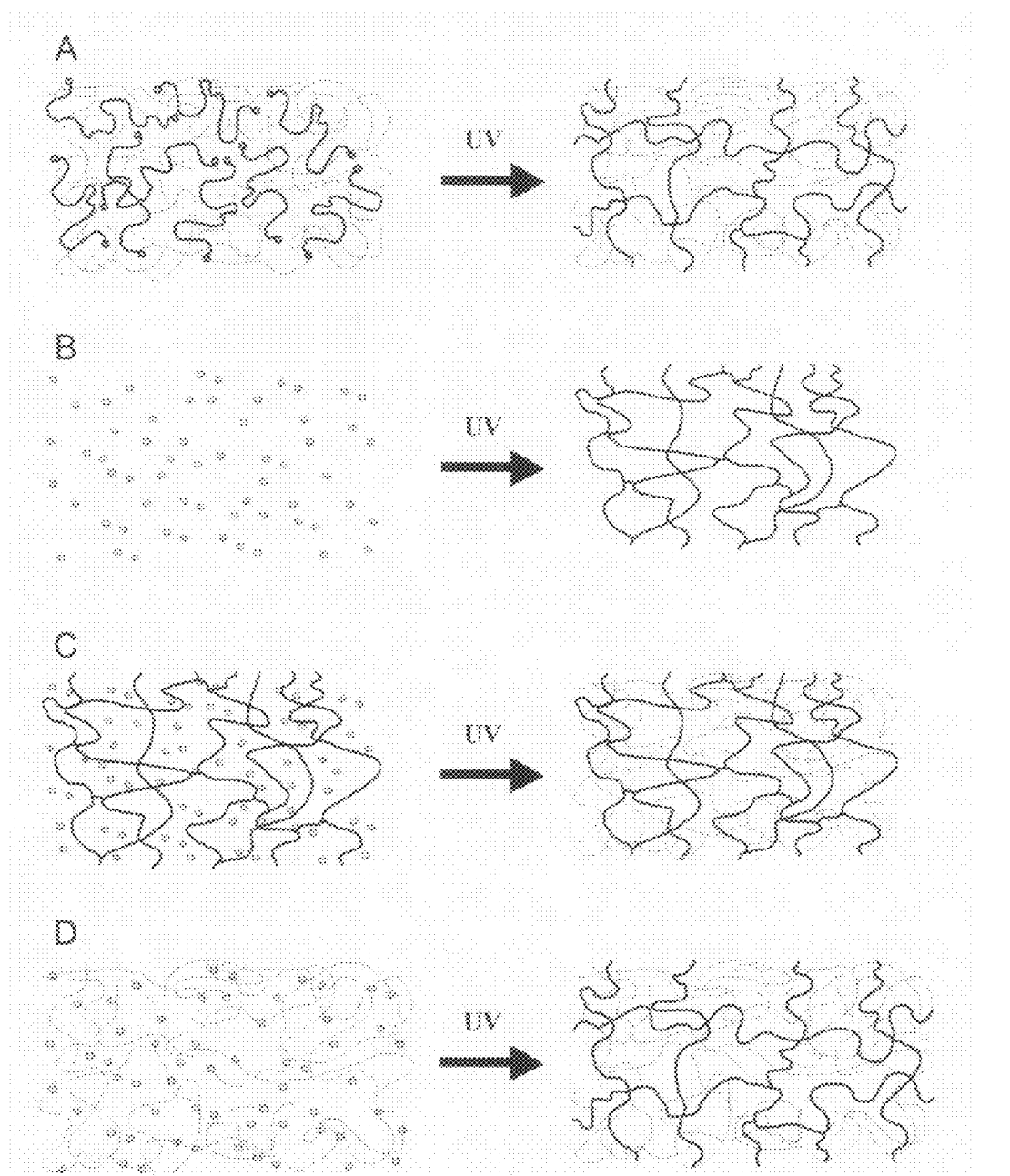
FIG. 3 A. shows according to an embodiment of the present invention method steps of forming a telechelic macromonomeric first network and linear macromolecules and/or biomacromolecules. A mixture of the first and second polymeric components is made, and then the telechelic macromonomers are reacted under UV light to form the first network in the presence of the second. If the second network is crosslinked chemically, then it is a fully interpenetrating network. If it is not (and only physically crosslinked), then it is a semi-interpenetrating network.
B. shows according to an embodiment of the present invention method steps of how a first network is formed from monomers (stars). Exposure to UV light in the presence of a photoinitiator and crosslinker (not shown) leads to polymerization and crosslinking to form a network.
C. shows according to an embodiment of the present invention method steps of how an IPN is formed from a monomer-based first network. The first network is swollen with the second network precursor monomers (stars), a crosslinking agent (not shown) and a photoinitiator (not shown). Exposure to UV light initiates polymerization and crosslinking of the second network in the presence of the first to form the IPN.
D. shows according to an embodiment of the present invention method steps of how an IPN is formed from monomer-based first network and linear macromolecules and/or biomacromolecules. A mixture of the monomers and macromolecules is made, and then the monomers are reacted under UV light to form the first network in the presence of the second. If the second network is crosslinked chemically, then it is a fully interpenetrating network. If it is not (and only physically crosslinked), then it is a semi-interpenetrating network.

FIG. 3A shows a schematic of how an IPN is formed from a telechelic macromonomeric first network and linear macromolecules and/or biomacromolecules. A mixture of the first and second polymeric components is made, and then the telechelic macromonomers are reacted under UV light to form the first network in the presence of the second. If the second network is crosslinked chemically, then it is a fully interpenetrating network. If it is not (and only physically crosslinked), then it is a semi-interpenetrating network.

FIG. 3B shows a schematic of how a first network is formed from monomers (stars). Exposure to UV light in the presence of a photoinitiator and crosslinker (not shown) leads to polymerization and crosslinking to form a network.

FIG. 3C shows a schematic of how an IPN is formed from a monomer-based first network. The first network is swollen with the second network precursor monomers (stars), a crosslinking agent (not shown) and a photoinitiator (not shown). Exposure to UV light initiates polymerization and crosslinking of the second network in the presence of the first to form the IPN.

FIG. 3D shows a schematic of how an IPN is formed from monomer-based first network and linear macromolecules and/or biomacromolecules. A mixture of the monomers and macromolecules is made, and then the monomers are reacted under UV light to form the first network in the presence of the second. If the second network is crosslinked chemically, then it is a fully interpenetrating network. If it is not (and only physically crosslinked), then it is a semi-interpenetrating network.

Preferably, the hydrophilic monomer in the second network is ionizable and anionic (capable of being negatively charged). In a preferred embodiment, poly(acrylic acid) (PAA) hydrogel is used as the second polymer network, formed from an aqueous solution of acrylic acid monomers. Other ionizable monomers include ones that contain negatively charged carboxylic acid or sulfonic acid groups, such as methacrylic acid, 2-acrylamido-2-methylpropanesulfonic acid, hyaluronic acid, heparin sulfate, chondroitin sulfate, and derivatives, or combinations thereof. The second network monomer may also be positively charged or cationic. The hydrophilic monomer may also be non-ionic, such as acrylamide, methacrylamide, N-hydroxyethyl acrylamide, N-isopropylacrylamide, methylmethacrylate, N-vinyl pyrrolidone, 2-hydroxyethyl methacrylate, 2-hydroxyethyl acrylate or derivatives thereof. These can be copolymerized with less hydrophilic species such as methylmethacrylate or other more hydrophobic monomers or macromonomers. Crosslinked linear polymer chains (i.e. macromolecules) based on these monomers may also be used in the second network, as well as biomacromolecules such as proteins and polypeptides (e.g. collagen, hyaluronic acid, or chitosan).

Adding a photoinitiator to an aqueous solution of the end-linkable macromonomers in water and exposing the solution to UV light results in the crosslinking of the PEG macromonomers, giving rise to a PEG hydrogel. Polymerizing and crosslinking a second network inside the first network will give rise to the IPN structure. Preparing IPN hydrogels through free-radical polymerization has the additional advantage that it will enable the use of molds to form hydrogels of desired shape. The free-radical polymerization can be initiated through UV irradiation—in which case transparent molds can be used—or through other means such as thermal-initiation in which non-transparent molds can be used. Preferably, the first polymer network contains at least 50%, more preferably at least 75%, most preferably at least 95% of the telechelic macromonomer by dry weight. Other solutions including buffers and organic solvents (or mixtures thereof) may also be used to dissolve the first network macromonomers or second network monomers.

Any type of compatible cross-linkers may be used such as, for example, ethylene glycol dimethacrylate, ethylene glycol diacrylate, diethylene glycol dimethacrylate (or diacrylate), triethylene glycol dimethacrylate (or diacrylate), tetraethylene glycol dimethacrylate (or diacrylate), polyethylene glycol dimethacrylate, or polyethylene glycol diacrylate, methylene bisacrylamide, N,N'-(1,2-dihydroxyethylene) bisacrylamide, derivatives, or combinations thereof. Any number of photoinitiators can also be used. These include, but are not limited to, 2-hydroxy-2-methyl-propiophenone and 2-hydroxy-1-[4-(2-hydroxyethoxy)phenyl]-2-methyl-1-propanone.

The following description refers to an exemplary embodiment of a strain-hardened interpenetrating polymer network hydrogel with PEG as a first network polymer and PAA as a second network polymer. The IPN hydrogel is synthesized by a (two-step) sequential network formation technique based on UV initiated free radical polymerization. A precursor solution for the first network is made of purified, telechelic PEG dissolved in phosphate buffered saline (PBS) solution, water, or an organic solvent with, either 2-hydroxy-2-methyl-propiophenone or 2-hydroxy-1-[4-(2-hydroxyethoxy)phenyl]-2-methyl-1-propanone as the UV sensitive free radical initiator. The types of telechelic PEG macromonomers used were PEG-diacrylate, PEG-dimethacrylate, PEG-diacrylamide, and PEG-diallyl ether. In other embodiments, either network can be synthesized by free radical polymerization initiated by other means, such as thermal-initiation and other chemistries not involving the use of ultraviolet light. In the case of UV polymerization, the precursor solution is cast in a transparent mold and reacted under a UV light source at room temperature. Upon exposure, the precursor solution undergoes a free-radical induced gelation and becomes insoluble in water. The mold is fabricated in such a way that yields hydrogels at equilibrium swelling desired dimensions.

To incorporate the second network, the PEG-based hydrogels are removed from the mold and immersed in the second monomer solution, such as an aqueous solution of (10-100% v/v) acrylic acid containing a photo-initiator and a cross-linker, from 0.1% to 10% by volume triethylene glycol dimethacrylate (TEGDMA), triethylene glycol divinyl ether, N,N-methylene bisacrylamide, and N,N'-(1,2-dihydroxyethylene)bisacrylamide, for 24 hours at room temperature. The swollen gel is then exposed to the UV source and the second network is polymerized and crosslinked inside the first network to form an IPN structure. Preferably, the molar ratio of the first network telechelic macromonomer to the second network monomer ranges from about 1:1 to about 1:5000. Also preferably, the weight ratio of the first network to the second network is in the range of about 10:1 to about 1:10. In another embodiment of the present invention, the IPNs have a molar ratio of the second monomer ingredient to the first macromonomer ingredient higher than 100:1.

Key characteristics of hydrogels such as optical clarity, water content, flexibility, and mechanical strength can be controlled by changing various factors such as the second monomer type, monomer concentration, molecular weight and UV exposure time.

A range of hydrogels of the preferred embodiment (PEG/PAA IPN) have been developed. Specifically, IPNs of PEG-diacrylate (PEG-DA) and poly(acrylic acid) from PEG of molecular weights 275 to 14000 have been synthesized. It was found that the low molecular weight PEG-DA (<1000) gave rise to gels that were opaque or brittle, whereas the hydrogels made from the higher molecular weight PEG-DA (>1000) were transparent and flexible. In addition, IPNs with PEG-dimethacrylate, PEG-diacrylamide, PEG-diallyl ether, and combinations of these (and with varying molecular weight) in the first network have been developed.

In one example, we fixed the concentration of PEG-DA (MW 3400-14000 Da) to 50% (wt/wt) in PBS for the first network and changed concentrations of acrylic acid from 15% (v/v) to 100% (v/v). The cross-linking density of the IPN hydrogel increased as molecular weight of PEG decreased and concentration of acrylic acid increased. We made a mechanically strong and transparent hydrogel when the concentration of acrylic acid was in the range of 20% (v/v) to 100% (v/v). In this range of concentration of acrylic acid, the weight ratio of first and second network was varied over a wide range.

Figure 4:
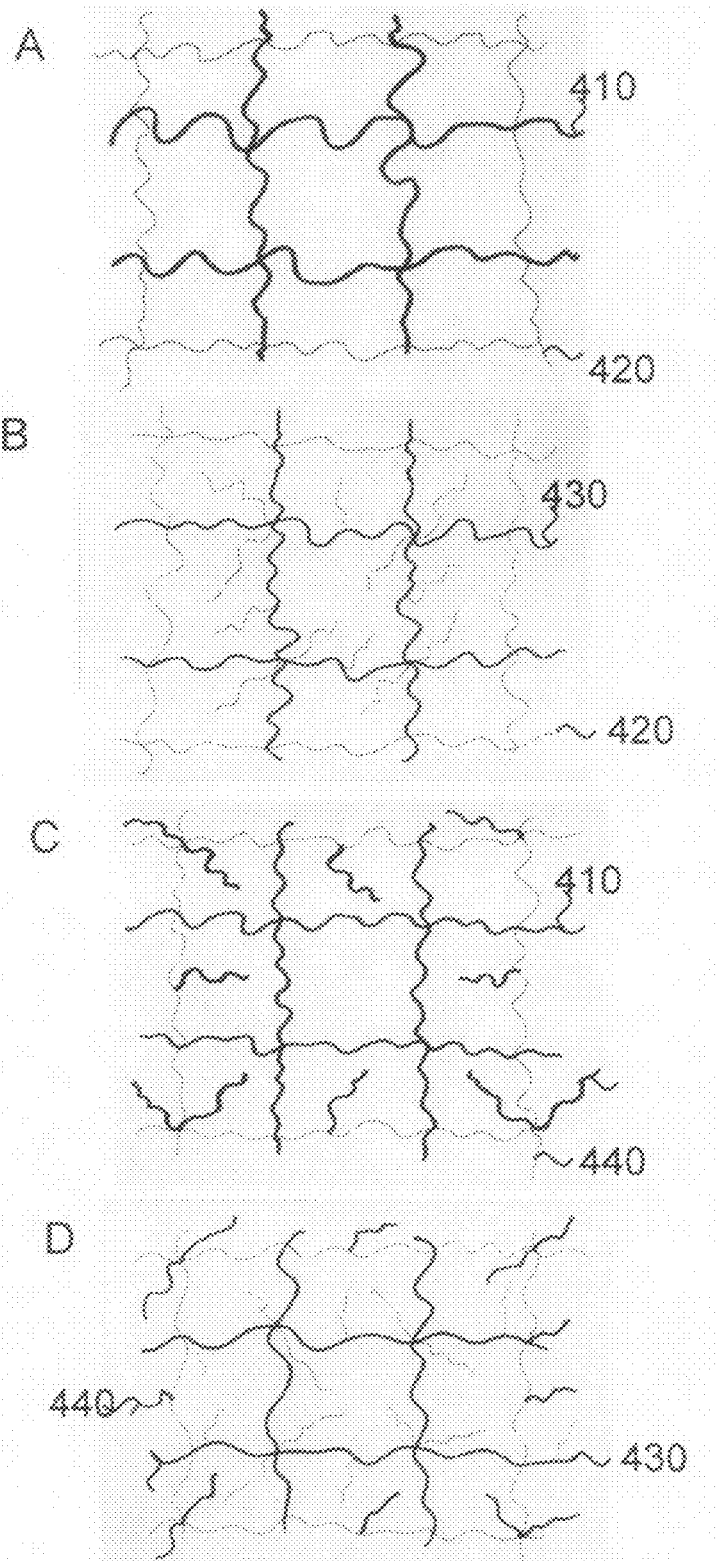
FIG. 4 shows according to embodiments of the present invention: (A) an IPN with two different polymers, differentiated by black lines (410) and grey lines (420), (B) an IPN with a graft-copolymer (430) of the two polymers in the first network and a homopolymer in the second network (420), (C) an IPN with a homopolymer (410) in the first network and a graft-copolymer of the two polymers in the second network (440), and (D) an IPN with graft-copolymers (430, 440) of the two polymers in both the first and the second networks.

In one embodiment of the present invention, grafted polymers are used to form the IPN. FIG. 4A shows a standard IPN according to the present invention, with first polymer network (black lines) and second polymer network (grey lines). FIG. 4B shows an IPN in which first polymer network is grafted with hydrophilic polymer. Any of the aforementioned macromonomers, monomers, or combinations of macromonomers and monomers may be used to get a grafted structure. FIG. 4C shows an IPN in which second polymer network is grafted with a hydrophilic macromonomer. FIG. 4D shows an IPN in which first polymer network is grafted with hydrophilic monomer and second polymer network is grafted with a hydrophilic macromonomer. The grafted networks are made by polymerizing aqueous mixtures of the two components in ratios that yield a network that is predominantly made from one polymer but has grafted chains of the second polymer.

Examples of First Network Telechelic Macromonomers

Figures 5, 6:
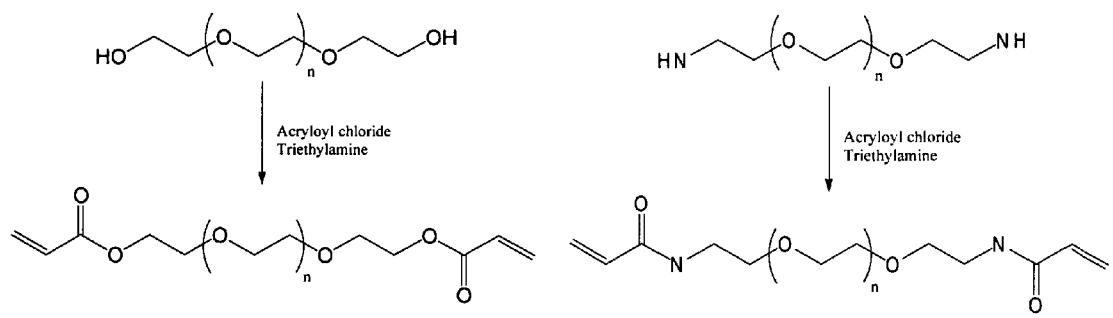
FIG. 5 shows according to an embodiment of the present invention a schematic of the synthesis of telechelic PEG-diacrylate from a PEG-diol macromonomer. To generate PEG-dimethacrylate, methacryloyl chloride would be reacted with the PEG-diol instead of acryloyl chloride.
FIG. 6 shows according to an embodiment of the present invention a schematic of the synthesis of telechelic PEG-diacrylamide from a PEG-diol macromonomer. To generate PEG-dimethacrylamide, methacryloyl chloride would be reacted with the PEG-diol instead of acryloyl chloride.

Telechelic PEG macromonomers with acrylate or methacrylate endgroups were synthesized in the following manner. PEG was dried from Toluene, redissolved in THF (per 100 g 550 mL) and kept under Nitrogen. Distilled Triethylamine (2.5 eq per OH group) was added slowly. Then acryloyl chloride (or methacryloyl chloride) was added via dropping funnel (diluted with THF) over 30 min, room temperature. The reaction (FIG. 5) was allowed to proceed overnight. Filtration was carried out to remove the formed salt. The volume of the solvent was reduced using a Rotavap, and precipitation was carried out in diethylether. As an alternative to extraction, filtration via cellulose membrane has also been performed. The raw product was dried after precipitation from diethylether in a vacuum, then dissolved in MeOH and dried in a Rotavap. It is then dissolved in water and filtrated through a membrane, and finally freeze-dried.

To attain a PEG-diacrylamide first network, the following procedure was followed. PEG mol wt 3400 (100 g, 58.8 mmol —OH) was azeotropically distilled in 700 mL toluene under nitrogen, removing about 300 mL of toluene. The toluene was then evaporated completely and then the PEG re-dissolved in anhydrous tetrahydrofuran. The triethylamine was distilled prior to use. The excess of Mesylchloride used was 3 eq per OH endgroup. The solution was cooled in a room temperature bath under Nitrogen and then cooled in an ice bath. Anhydrous dichloromethane (Aldrich) was added until the solution became clear (about 100 mL). Triethylamine (24.6 mL, 176.5 mmol, Aldrich) was then added dropwise with stirring, followed by the dropwise addition of 13.65 mmol mesyl chloride (176.5 mmol, Aldrich). The reaction proceeded overnight under argon. The solution was filtered through paper under vacuum until clear, followed by precipitation in diethyl ether. The product was then collected by filtration and dried under vacuum. The PEG-dimesylate product was added to 400 mL 25% aqueous ammonia solution in a 1 L bottle. The lid was tightly closed and sealed with Parafilm, and the reaction was vigorously stirred for 4 days at room temperature. The lid was then removed and the ammonia allowed to evaporate for 3 days. The pH of the solution was raised to 13 with 1 N NaOH, and the solution was extracted with 100 mL dichloromethane. For the extraction with dichloromethane, NaCl was added to the water-phase (~5 g) and the water-phase was extracted several times with 150 mL of dichloromethane. The dichloromethane washes were combined and concentrated in vacuo. The product was precipitated in diethyl ether, and dried under vacuum: PEG-diamine mol wt 3400 (20 g, 11.76 mmol amine) was then azeotropically distilled in 400 mL of toluene under Nitrogen, removing about 100 mL of toluene. The toluene was then evaporated completely and then the PEG re-dissolved in anhydrous tetrahydrofuran. The solution was cooled in a room temperature bath under Nitrogen and then cooled in an ice bath. Anhydrous dichloromethane (Aldrich) was added until the solution become clear, about 50 mL. Triethylamine (2.46 mL, 17.64 mmol, Aldrich) was added dropwise with stirring, followed by the dropwise addition of 1.43 mL of acryloyl chloride (17.64 mmol). The reaction (FIG. 6) proceeded overnight in the dark under Nitrogen. The solution was then filtered through paper under vacuum until clear, followed by precipitation in diethyl ether. The product was collected by filtration and dried under vacuum. The product was then dissolved in 200 mL of deionized water, with 10 g of sodium chloride. The pH was adjusted to pH 6 with NaOH and extracted 3 times with 100 mL of dichloromethane (with some product remaining in the water phase as an emulsion). The dichloromethane washes were combined and the product was precipitated in diethyl ether, and dried under vacuum. Alternatively, PEG-diacrylamide has been precipitated from Diethylether once, redissolved in MeOH, dried from MeOH and then purified by centrifugal filtration in water through a cellulose membrane (MWCO: 3000). Freeze drying was used to attain the desired product.

Figure 7:
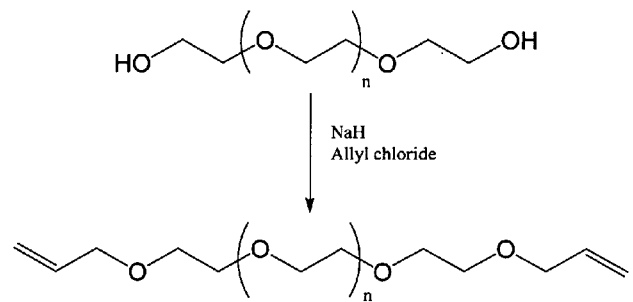
FIG. 7 shows according to an embodiment of the present invention a schematic of the synthesis of telechelic PEG-allyl ether from a PEG-diol macromonomer.

Macromonomers containing diols can be converted into allyl ethers. Difunctional allyl ether macromonomers were synthesized from (PEG) using the following procedure. Fresh anhydrous tetrahydrofuran (THF) (100 mL) was added to every 10 g of PEG (Aldrich). This mixture was gently heated until the PEG dissolved and then cooled in an ice bath before sodium hydride (Aldrich) was slowly added in multiple portions (1.05 molar equiv. NaH for the PEG ReOH groups). After the release of $H_2$ gas ceased, the system was purged with argon and allyl chloride or allyl bromide (1.1 molar equiv. per PEG OH-group, diluted 1:10 in THF) was added dropwise using an addition funnel, after which the reaction mixture (FIG. 7) was transferred to an 85 degrees Celsius oil bath and refluxed overnight. Vacuum filtration was used to remove the sodium bromide side products and rotary evaporation was used to reduce the concentration of THF before the PEG-allyl ether products were precipitated from solution using iced diethyl ether (Fisher Scientific, 10:1 v:v diethyl ether:THF solution).

Strain-Hardening

The following pertains to studies performed by the inventors on the relationship between the network structure and the mechanical properties of PEG/PAA IPN hydrogels with acrylate crosslinking in the first network and triethylene glycol dimethacrylate crosslinking in the second network as an exemplary embodiment. Hydrogels based on poly(ethylene glycol) (PEG) and poly(acrylic acid) (PAA) have properties such as biocompatibility, hydrophilicity, transparency, permeability, and resistance to protein adsorption, all of which are advantageous in a variety of biomedical applications. PEG, for instance, is widely utilized as a surface coating for intravenous and intraperitoneal catheters due to its ability to prevent the adhesion of thrombogenic and immunogenic proteins. PAA is an ionizable polymer ($pK_a$=4.7) that is the absorbent material. In addition, it undergoes large volume changes in response pH changes. At a pH greater than 4.7, the PAA network is negatively charged and swollen. At a pH lower than 4.7, the PAA network is protonated and contracted. To date, however, the relative fragility of both PEG and PAA has precluded them from serving as the primary material for tissue replacement or augmentation applications that require high mechanical strength.

This present invention is based on loosely crosslinking PAA within a preexisting, highly crosslinked neutral PEG network results in an IPN with unusually high mechanical strength. Moreover, these PEG/PAA IPNs were found to exhibit very different mechanical behavior in pure water and buffered saline, indicating that both pH and salt concentration play important roles in defining the relative network configuration. The controllable swelling of PAA within the confines of the more rigid, neutral PEG network provided a convenient first step for studying the effect of relative chain configuration and topological interactions on the properties of the IPN. The use of defined, telechelic macromonomers in the first network facilitated tuning of the mesh size of the first network while placing a three-dimensional constraint on the swelling of the second network.

The experimental focus of this section is on the strain hardening observed in this system by testing how it manifests through uniaxial tensile tests under various conditions of first and second network crosslinking and swelling. Swelling data were used to calculate the equilibrium water and polymer content of the networks, which were correlated with Young's modulus, true stress-at-break, and true strain-at-break. The results indicate that strain hardening is derived from physical entanglements between the PEG and PAA networks that are intensified by bulk deformation. Under conditions that promote hydrogen bonding (when the pH is at or below 4.7, the $pK_a$ of PAA), these entanglements are reinforced by inter-polymer complexes between PEG and PAA, leading to an increase in the fracture strength of the IPN. Under conditions that promote ionization of PAA (when the pH is above 4.7), increased steric interactions (i.e. physical crosslinks) between the swelling PAA network and static, telechelic PEG macromonomer network lead to a dramatic increase in Young's modulus.

Hydrogel Synthesis and Swelling

All hydrogels were formed by photopolymerization with UV light using the water-soluble photoinitiator, 2-hydroxy-2-methyl-propiophenone. Before the IPNs were prepared, single network hydrogels based on PEG and PAA were synthesized separately to confirm the formation of gels of each composition and to investigate the physical properties of the single networks. For the PEG single network, a range of hydrogels that varied between 275 and 14000 for the MW of the PEG macromer was synthesized. It was found that low MW PEG macromonomers gave rise to gels that were transparent but brittle, whereas the hydrogels made from higher molecular weight PEG-DA (3400) were transparent and flexible when swollen in deionized water.

Based on these results, a range of different MWs of PEG (3400, 4600, 8000, and 14000) were chosen as macromonomers for the first hydrogel network. A series of IPNs was synthesized by polymerizing and crosslinking a PAA network within each type of PEG network. The resultant IPNs were transparent and had significantly greater mechanical strength compared with single network hydrogels.

Effect of Changing the MW of the PEG-DA Macromonomer

To explore the effect of the molecular weight of the telechelic PEG-DA macromonomer on IPN mechanical strength, PEG chains with MWs 3400 Da, 4600 Da, 8000 Da, and 14000 Da were used in the first network while keeping the acrylic acid polymerization conditions constant (50% v/v in deionized water with 1% v/v crosslinker and 1% v/v photoinitiator with respect to the monomer). The resulting IPNs were characterized in terms of their water content, tensile properties, and mesh size in deionized water.

Figure 8:
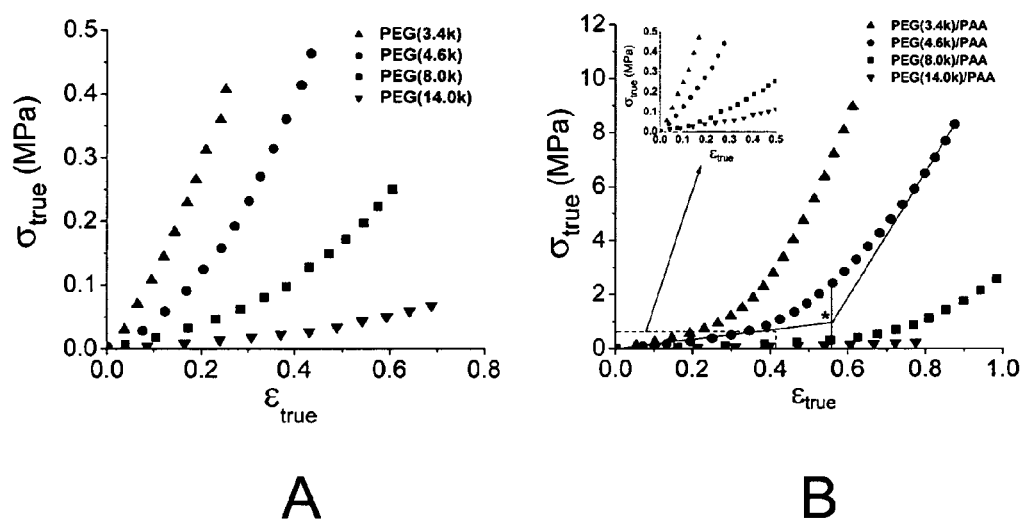
FIG. 8 A. shows according to an embodiment of the present invention true stress versus true strain curves for PEG-DA single networks of MW 3400 (▲), 4600 (●), 8000 (■), and 14000 (▼).
B. shows according to an embodiment of the present invention true stress versus true strain curves for PEG/PAA IPNs with PEG MW 3400 (▲), 4600 (●), 8000 (■), and 14000 (▼). The intersection (*) between the initial and final tangents to each curve defines the critical strain ($\epsilon_{crit}$) for strain hardening in each IPN.

Changing the MW of the PEG-DA macromonomer led to a change in the moduli of the PEG-DA single networks, as shown in FIG. 8A. This effect was magnified in the PEG/PAA IPNs (FIG. 8B), where the IPNs initial and final moduli get increasingly higher as the networks are prepared from lower molecular weight PEG-DA macromonomers.

Of note, there was little increase in strength when the PEG MW is increased above 8000, indicating that a contrast between the molecular weight between crosslinks of the PEG and PAA networks is important for strength enhancement. Moreover, the molecular weight of the PEG macromonomer was strongly correlated to the critical strain ($\epsilon_{crit}$) at which the stress-strain curve makes the transition from the initial modulus to the strain-hardened final modulus (FIG. 8B). The $\epsilon_{crit}$ was smaller for the IPNs prepared from lower MW PEG macromonomers, meaning that these networks strain-harden more rapidly in response to deformation.

Figure 9:
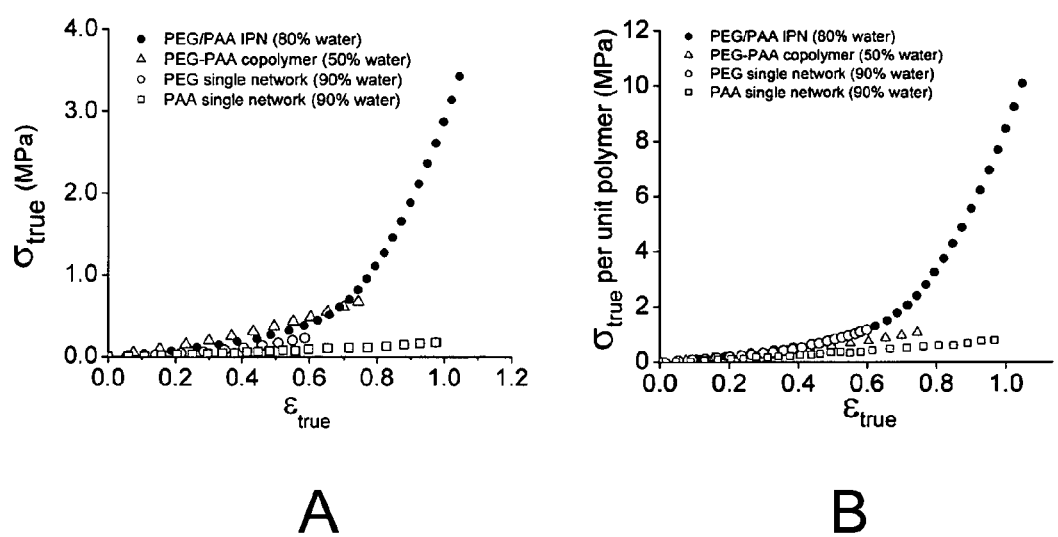
FIG. 9 A. shows according to an embodiment of the present invention true stress-true strain curves for PEG(8.0k)/PAA IPN, PEG(8.0k)-PAA copolymer, PEG(8.0k), and PAA networks.
B. shows according to an embodiment of the present invention normalized true stress-true strain curves for PEG (8.0k)/PAA IPN, PEG(8.0k)-PAA copolymer, PEG (8.0k), and PAA networks.

The significance of forming an interpenetrating structure rather than a copolymeric structure was explored by synthesizing a PEG-co-PAA copolymer hydrogel and testing its tensile properties. Its stress-strain profile was then juxtaposed with those of the IPN and the PEG and PAA single networks. In FIG. 9A, a representative true stress ($\sigma_{true}$) versus true strain ($\epsilon_{true}$) profile of the PEG(8.0k)/PAA IPN is compared to those of the PEG(8.0k)-PAA copolymer and their component PEG(8.0k) and PAA networks. The IPN exhibits strain-hardening behavior with a stress-at-break that is greater than four times that of the copolymer and single network. However, since each of the materials tested has different water content, the stress data were normalized on the basis of polymer content to determine the true stress per unit polymer in each hydrogel.

In FIG. 9B, the true stress per unit polymer ($\sigma_{true}$ per unit polymer) is plotted against true strain for PEG(8.0k)-DA, PAA, PEG(8.0k)/PAA, and the PEG(8.0k)-PAA copolymer. The initial moduli of the PEG single network, the copolymer, and IPN are identical ($E_o$ per unit polymer=0.91 MPa), while that of the PAA single network is lower ($E_o$ per unit polymer=0.55 MPa). Near the break point of the PEG network, $\epsilon_{true}$~0.6, the copolymer continues to be elongated with a modulus that is intermediate between the PEG and PAA single networks, of which it is equally composed by weight. Ultimately, it fails at a strain that is also intermediate between the $\epsilon_{break}$ values of the two single networks. In stark contrast, just beyond the failure point of the PEG network, the PEG/PAA IPN manifests a dramatic strain hardening effect in which its modulus increases by 30 fold, and breaks at $\epsilon_{true}$~1.0 under a mean maximum stress per unit solid of 10.6 MPa. Without normalization for polymer content, $\sigma_{break}$ for the IPN (20% solid) and copolymer (51% solid) are 3.5 MPa and 0.75 MPa, respectively.

pH Dependence of IPN and PAA Physical Properties

To explore the role of interpolymer hydrogen bonding, the pH of the hydrogel swelling liquid was varied to change the ionization state of the PAA network. Since the equilibrium swelling of PAA is sensitive to variations in pH, a change in the pH was expected to have an impact on the mechanical properties of PEG/PAA IPNs. After synthesis, the water-swollen PAA single networks and PEG(8.0k)/PAA IPNs were placed in buffers of pH 3-6 and constant ionic strength (I) of 0.05. In both the PAA network and the IPN, the equilibrium water content increased as the pH was increased from 3 to 6 (FIG. 10a-c, upper plots) In the case of the PAA networks, those at pH 3 and 4 were moderately swollen, while those at pH 5 or 6 were highly swollen due to ionization of PAA above its $pK_a$ (4.7). The IPNs also achieved different levels of swelling depending on the pH; those at pH 3 and 4 were moderately swollen, while those at pH 5 or 6 were highly swollen due to ionization of PAA above its $pK_a$ (4.7). Of note, at both pH 3 and 4, the IPN achieved a lower equilibrium water content than PAA alone. This can be explained, in part, by the fact that PEG and PAA complex with each other via hydrogen bonds in an acidic environment, leading to a more compact, less hydrated interpenetrating network structure. At pH above 4.7, the PEG and PAA chains dissociate as the PAA becomes ionized and counterions (along with water) enter the hydrogel to maintain charge neutrality, leading to a high degree of swelling. Nevertheless, the IPNs swell to a slightly lower extent (1.0-1.5%) than the PAA single networks due to the constraint that the PEG network places on PAA swelling.

Figure 10:
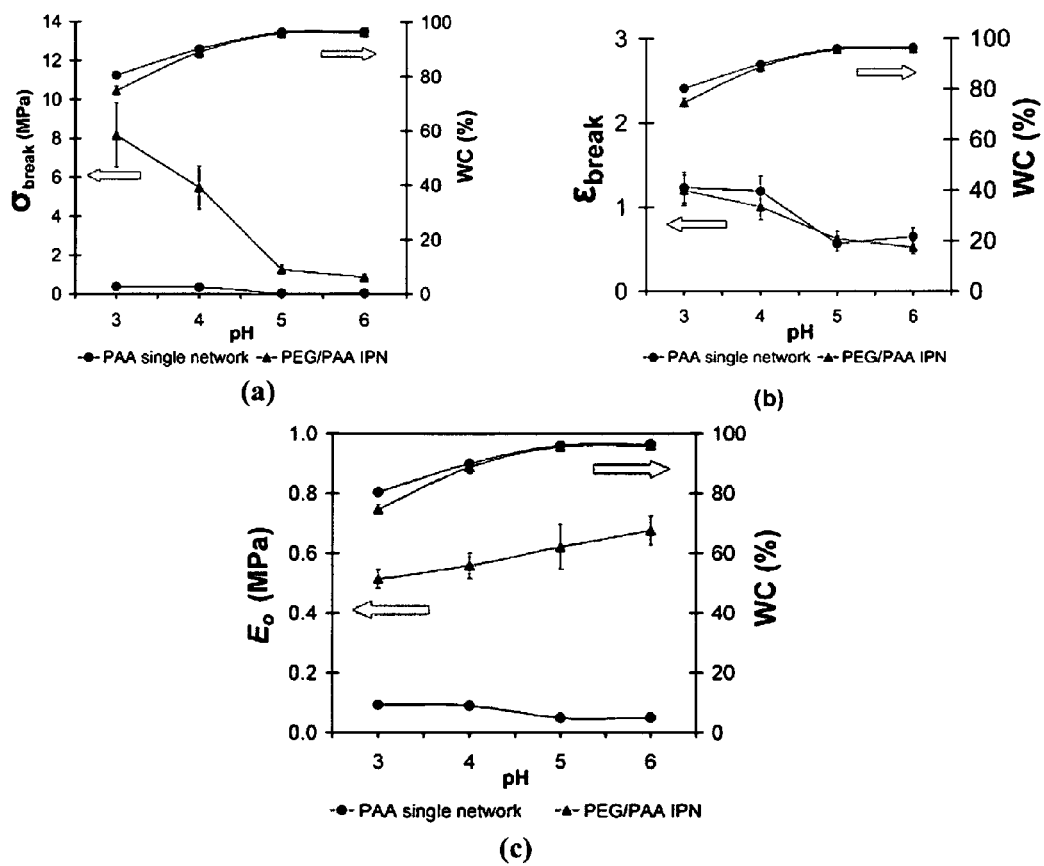
FIG. 10 shows according to an embodiment of the present invention: (a) pH-dependence of the stress at break ($\sigma_{break}$) and water content for PEG(8.0k)/PAA IPNs and PAA single networks, (b) pH-dependence of the strain at break ($\epsilon_{break}$) and water content for PEG(8.0k)/PAA IPNs and PAA single networks, (c) pH-dependence of the initial modulus ($E_o$) and water content for PEG(8.0k)/PAA IPNs and PAA single networks.

FIG. 10a also shows that the stress-at-break ($\sigma_{break}$), or tensile strength, of the PEG/PAA IPN is nearly an order of magnitude greater in its less-swollen state at pH 3 ($\sigma_{break}$=8.2 MPa) than in its more swollen state at pH 6 ($\sigma_{break}$=0.86 MPa). A similar phenomenon is observed in the PAA network, but the absolute values for $\sigma_{break}$ are only 0.38 MPa at pH 3 and 0.05 MPa at pH 6. At every pH, then, the IPN has greater tensile strength than the PAA network, and this difference is intensified at lower pH.

In contrast to the differences in the stress-at-break, the trends in the strain-at-break values of the IPN and PAA networks are roughly equivalent (FIG. 10b), changing from $\epsilon_{break}$ values of ~1.2 at pH 3 to ~0.55 at pH 6. This result confirms the observation made in FIGS. 9a-b, in which the extensibility of the IPN seems to be due to the presence of the PAA network, which has a higher $\epsilon_{break}$ (0.9) than PEG (0.6). The mere presence of the PAA network in the IPN appears to enhance the uniaxial extensibility of the network. In the context of the stress-at-break data (FIG. 10a), however, the load-bearing capacity at higher extensions is dramatically greater in the presence of hydrogen bonding at low pH than it is in the absence of hydrogen bonding at high pH.

In contrast, FIG. 10c indicates that the pH dependence of the initial Young's moduli ($E_o$) of the IPN and PAA networks is less straightforward. The modulus of the PAA network exhibits a small drop from 0.09 MPa to 0.05 MPa as the pH is increased from 3 to 6. On the other hand, the modulus of the IPN does not decrease at all, but rather increase when the pH is changed from 3 to 6. Of note, the pH-dependence of the IPN does not follow the trend exhibited by the PAA single network, in which the modulus drops by approximately one-half when transitioning from pH 4 to pH 5. This decrease in modulus is correlated with an increase in water content of the PAA single network (FIG. 10c, upper plots). Moreover, the apparent preservation of the modulus in the IPN despite an increase in water content and loss of hydrogen bonding is paradoxical in the context of the sharp declines observed in the break and $\sigma_{break}$ values.

Figure 11:
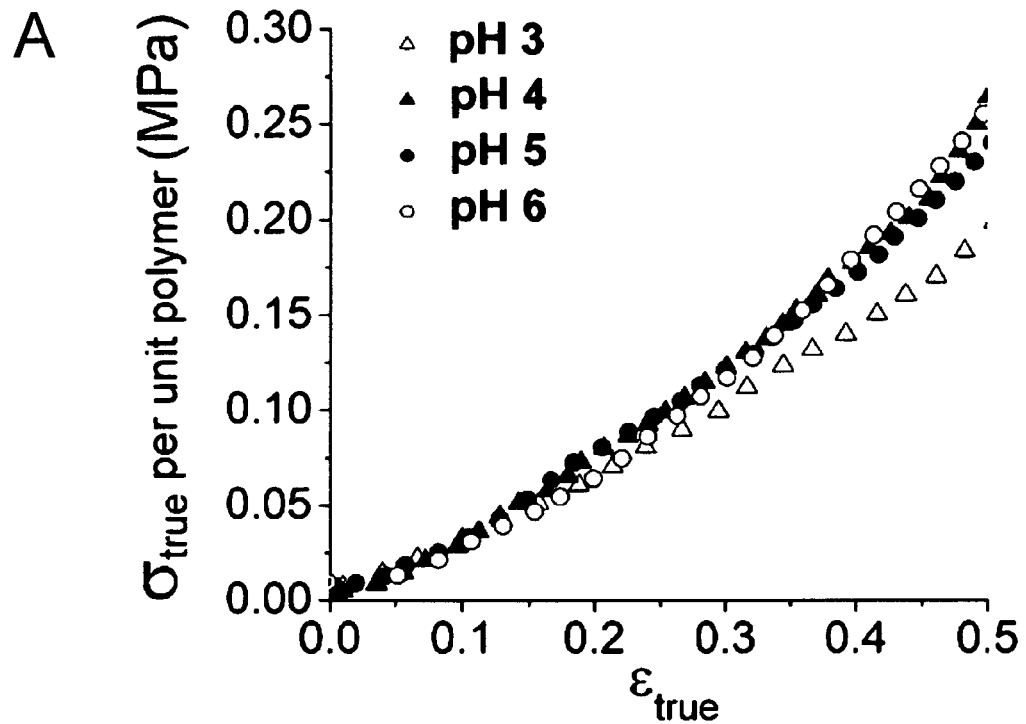
FIG. 11 shows according to an embodiment of the present invention: A. true stress per unit polymer versus true strain curves for PAA in pH 3-6, B. true stress per unit polymer versus true strain curves for PEG(8.0k)/PAA in pH 3-6.
Figure 11:
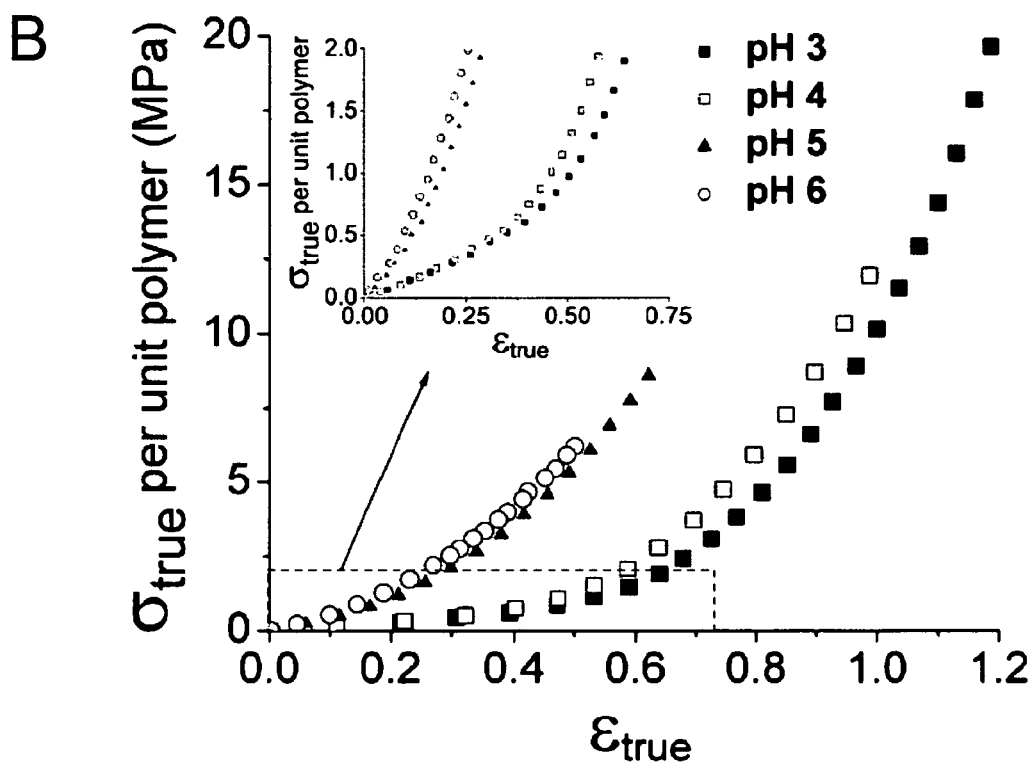

The strain-hardening per unit polymer is shown in the stress-strain profiles in FIGS. 11A and 11B. FIG. 11A plots the true stress per unit polymer versus strain in the PAA gels. In contrast to the non-normalized data in which the initial modulus of PAA at pH 3-4 is higher than it is at pH 5-6 (not shown), the initial moduli of PAA at all pHs converge when the stress data are corrected for differences in polymer content. This indicates that the reduction in mechanical strength that accompanies an increase in pH in PAA networks is largely due to the swelling of the network. Correcting the stress data for polymer content in the IPNs yields the graph shown in FIG. 11B. In this plot, the difference in the onset of strain hardening between the low pH and high pH regimes is accentuated. The stress-strain curves of the high pH IPNs proceed beyond their uncorrected maximum stresses and end parallel to those of the low pH regimes. This result suggests that, while the more swollen IPNs have lower tensile strength, this may be a side effect of the accelerated strain hardening that leads to greater load bearing at smaller strains (due to a higher modulus), and, in turn, an earlier strain-at-break.

To investigate the consequence of relative network moduli even further, the swelling of PAA within the IPNs was maximized. The experimental data shown in FIG. 10c indicated that the modulus of the IPN was not negatively affected by the increased swelling. We hypothesized that the PEG network acts as a constraint on the swelling of PAA in a way that leads to additional interpolymer interactions and a corresponding increase in the IPN modulus. In particular, we postulated that increasing the constraining effect of the neutral PEG network on PAA swelling would increase the intensity and number of physical entanglements in the IPN and, in turn, lead to the strain hardening behavior observed in the IPN.

To test this hypothesis, the IPNs with first network MW PEG 3400, 4600, and 8000 and constant PAA network conditions were placed in phosphate buffered saline (PBS, pH 7.4, I=0.15) in order to induce maximal swelling under physiologic conditions.

Table 1 shows the equilibrium water content and corresponding swelling ratios for networks prepared from PEG macromonomers with each of these molecular weights, juxtaposed with the water content of the water-swollen and PBS-swollen IPNs. Increasing the size of the first PEG network from 3400 Da to 4600 Da and 8000 Da increases the degree to which the IPN is able to swell.

TABLE 1

Equilibrium water content (%) and swelling ratio (q)* of PEG and PAA single networks and PEG/PAA IPNs under varying swelling conditions.

| Specimen | Conditions | Water Content (%) | Swelling Ratio (q) |
| --- | --- | --- | --- |
| PAA | dH$_2$0** | 90.0 ± 1.7 | 10.0 |
| PAA | pH 7.4, I = 0.15 | 95.5 ± 1.7 | 22.1 |
| PEG(3.4k) | dH$_2$0 | 79.3 ± 2.1 | 4.8 |
| PEG(3.4k)/PAA | dH$_2$0 | 56.3 ± 3.3 | 2.4 |
| PEG(3.4k)/PAA | pH 7.4, I = 0.15 | 68.7 ± 1.6 | 3.2 |
| PEG(4.6k) | dH$_2$0 | 84.5 ± 0.4 | 6.5 |
| PEG(4.6k)/PAA | dH$_2$0 | 57.0 ± 0.6 | 2.3 |
| PEG(4.6k)/PAA | pH 7.4, I = 0.15 | 77.0 ± 1.2 | 4.4 |
| PEG(8.0k) | dH$_2$0 | 90.5 ± 1.2 | 10.5 |
| PEG(8.0k)/PAA | dH$_2$0 | 80.2 ± 1.5 | 5.1 |
| PEG(8.0k)/PAA | pH 7.4, I = 0.15 | 90.9 ± 0.1 | 11.0 |

*q = W$_s$/W$_d$ = ratio of swollen weight and dry weight.
**dH$_2$0 = deionized water Specifically, while the PEG(3.4k)/PAA IPN swells to only 70% water when ionized, the PEG(4.6k)/PAA IPN swells to 77% water and the PEG(8.0k)/PAA IPN swells to 90% water (nearly the same water content as the PEG(8.0k) single network) when ionized. Of note, the equilibrium water content values of the PEG(3.4k) and PEG(4.6k)-based IPNs do not approach those of their component PEG-DA networks (79.3% and 84.5%, respectively).

Figure 12:
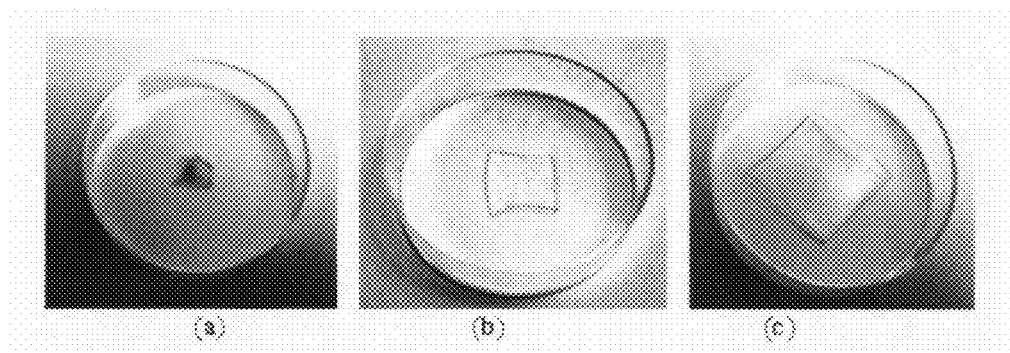
FIG. 12 shows according to an embodiment of the present invention show a PEG/PAA hydrogel in (a) the dry state, (b) the partially-swollen state, and (c) the fully, equilibrium-swollen state.
Figure 13:
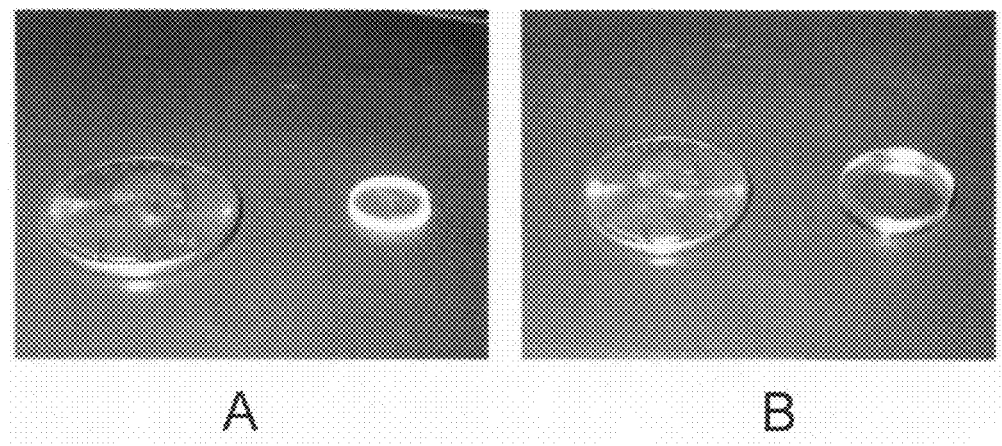
FIG. 13 shows according to an embodiment of the present invention: A. appearance of a PEG/PAA IPN based on PEG MW 4600 in the dried state. B. appearance of the PEG/PAA IPN shown in FIG. 13A after being immersed for 40 minutes in PBS, pH 7.4.

FIGS. 12a-c show a PEG/PAA hydrogel in (a) the dry state, (b) the partially-swollen state, and (c) the fully, equilibrium-swollen state. These photographs were taken by drying the hydrogel in a dessicator, then placing it in deionized water, and then removing it and patting it dry before taking pictures. FIGS. 13A-B shows a disc-shaped PEG/PAA hydrogel next to a coin in (d) the dried state, and (e) the swollen state, after being immersed in phosphate buffered saline (pH 7.4) for 40 minutes.

The water content of the hydrogels was evaluated in terms of the swollen-weight-to-dry-weight ratio. The dry hydrogel was weighed and then immersed in water as well as phosphate buffered saline. At regular intervals, the swollen gels were lifted, patted dry, and weighed until equilibrium was attained. The percentage of equilibrium water content (WC) was calculated from the swollen and dry weights of the hydrogel:

$$WC = \frac{W_s - W_d}{W_s} \times 100$$

where W$_s$ and W$_d$ are the weights of swollen and dry hydrogel, respectively.

Figure 14:
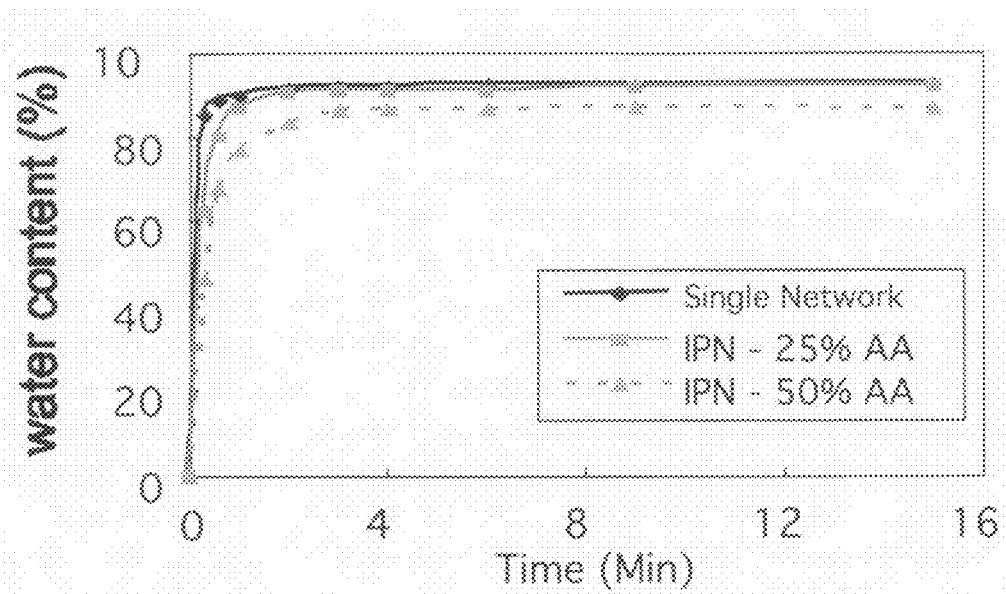
FIG. 14 shows according to an embodiment of the present invention time-dependence of the water content of a single network PEG hydrogels and PEG/PAA IPNs with different amounts of acrylic acid (AA) at the time of polymerization. The hydrogels were placed in deionized water in the dry state at time=0 and then weighed at regular intervals.

FIG. 14 shows the time-dependent swelling behavior of an IPN hydrogel composed of PEG and two different amounts of acrylic acid in the second network (25% and 50%). The single network IPN gels were dried in a desiccator, placed in deionized water, and then weighed at regular time intervals. In both hydrogels, the majority of swelling took place within 5-10 minutes and equilibrium swelling was achieved within 30-40 minutes.

The parameters varied to obtain hydrogels with differing water content were the molecular weight of the PEG macronomonomer, the weight fraction of PAA in the second network, as well as the amount of crosslinking agent (e.g. triethylene glycol dimethacrylate, or low molecular weight PEG-DA) added to the first or second networks.

Table 2 shows the effect of varying the concentration of acrylic acid monomer used to prepare the second network on the equilibrium water content of PEG/PAA IPNs. In general, lower concentrations of acrylic acid monomer leads to hydrogels with higher equilibrium water content.

TABLE 2

Equilibrium Water Content of PEG(8.0k)/PAA hydrogels with varying preparation concentration of acrylic acid (AA) monomer

| Concentration of AA in the preparation state | Equilibrium Water Content of PEG/PAA IPN |
|---|---|
| 30% | 99% |
| 40% | 91% |
| 50% | 83% |

Hydrogels according to the present invention made from these hydrogels, preferably have an equilibrium water content of between about 15%-95% and more preferably between about 50%-90%.

Because different MWs of PEG and different starting concentrations of acrylic acid result in different amounts of equilibrium water content, the final amount of PEG and PAA in the hydrogel varies depending on the MW of the starting PEG used and the concentration of acrylic acid used. Examples of compositions of varying weight ratios of PEG and PAA that have been made according to the present invention are shown in Table 2. The compositions in this table were all made using a starting concentration of 50% PEG macromonomers in water.

TABLE 3

Compositions of PEG(8.0k)/PAA IPNs with varying preparation concentration of AA monomer

| Concentration of AA in the preparation state | Dry Wt. % PEG in IPN | Dry Wt. % PAA in IPN | (Dry Wt.PEG)/ (Dry Wt. PAA) |
|---|---|---|---|
| 30% | 23.5% | 76.5% | 0.30 |
| 40% | 17.5% | 82.5% | 0.20 |
| 50% | 13.0% | 87.0% | 0.15 |

Figure 15:
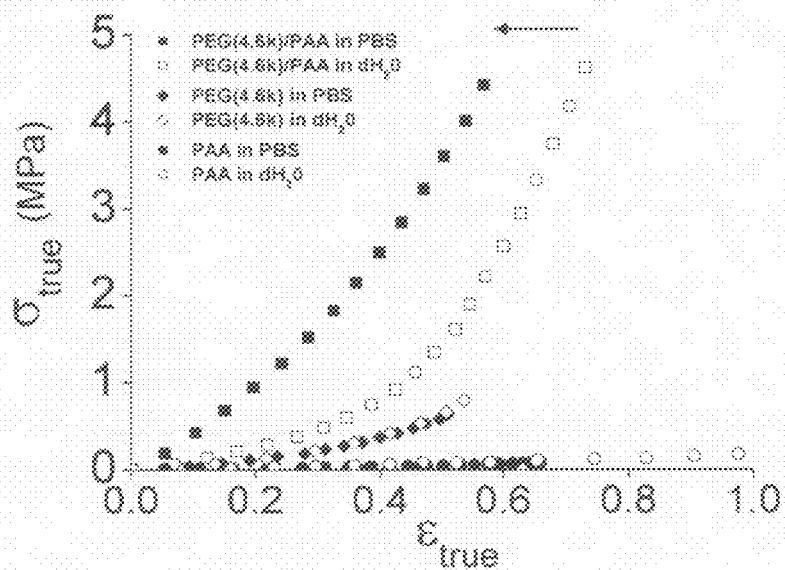
FIG. 15 shows according to an embodiment of the present invention true stress versus true strain curves of the PEG (4.6k)/PAA IPN in PBS and deionized water, as well as the PEG and PAA single networks in PBS and deionized water. The PEG(4.6k) network is unaffected by the change from water to PBS. The arrow indicates the shift in the stress-strain profile of the IPN after it has been strain-hardened by swelling to equilibrium in PBS.

We found that swelling of the PAA network within the confines of a more densely crosslinked PEG network (by lowering the MW of the PEG macromonomer) has dramatic consequences on the resulting IPN modulus. Specifically, FIG. 15 shows that the accelerated strain hardening due to elevated pH, as demonstrated in FIG. 11b, is accentuated even further when a PEG network with lower MW (4600 rather than 8000) is used to constrain PAA. These more tightly crosslinked IPNs were placed in phosphate buffered saline to examine them under physiologic conditions (pH 7.4, ionic strength=0.15) where the PAA network is greater than 99% ionized. The PEG(4.6k)/PAA IPN was first swollen to equilibrium in pure deionized water (pH 5.5, salt-free); it was then switched to the ionizing conditions of phosphate buffered saline (pH 7.4, I=0.15) and again swollen to equilibrium. The increase in the pH to 7.4 and the addition of salt caused the PAA network (but not the PEG network) to swell. The result of this differential swelling within the IPN was a dramatic upward shift in the stress-strain profile that included the initial portion of the curve. In other words, there was an increase in not only the rate of strain hardening, but also in the initial modulus.

Effects of Alternate Crosslinking in the IPN

Figure 16:
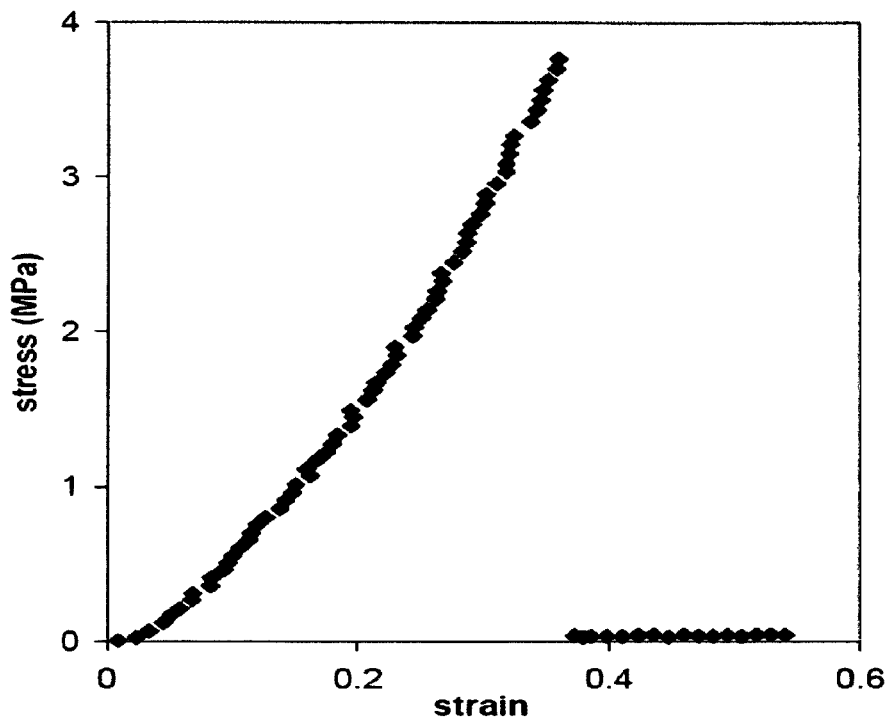
FIG. 16 shows according to an embodiment of the present invention the stress-strain profile of a PEG/PAA IPN prepared from a PEG-diacrylamide first network and a PAA second network crosslinked with N,N'-(1,2-dihydroxyethylene) bisacrylamide and swollen to equilibrium in PBS at pH 7.4. The strain-hardened mechanical properties of this IPN are similar to those of acrylate-based IPN system in FIG. 15.

FIG. 16 shows according to an embodiment of the present invention the stress-strain profile of a PEG/PAA IPN prepared from a PEG-diacrylamide first network and a PAA second network crosslinked with N,N'-(1,2-dihydroxyethylene) bisacrylamide and swollen to equilibrium in PBS at pH 7.4. The strain-hardened mechanical properties of this IPN are similar to those of acrylate-based IPN system in FIG. 15. These results demonstrated that alternate crosslinking strategies can be employed to create the strain-hardened IPNs based on telechelic macromonomer-based first networks and ionized second networks without deviating from the essence of the present invention.

Ionic Strength Effects

Figure 17:
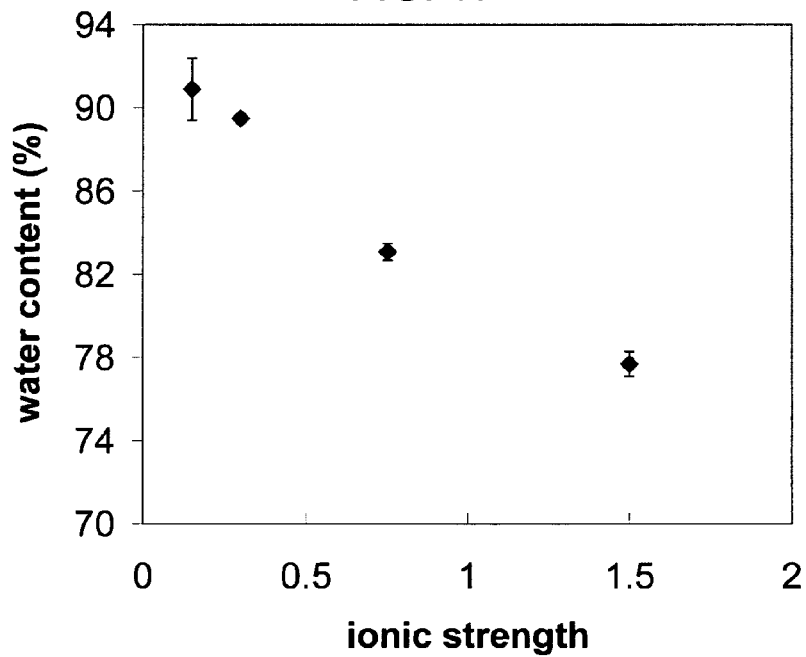
FIG. 17 shows according to an embodiment of the present invention effect of ionic strength on the water content of the PEG(8k)/PAA IPN

PEG/PAA IPNs were swollen to equilibrium in a series of PBS solutions of varying ionic strength (0.15 M, 0.30 M, 0.75 M, and 1.5 M) and their equilibrium water content and stress-strain properties were measured. FIG. 17 shows that the water content of the IPN is reduced with higher salt concentration in the swelling medium, from over 90% at I=0.15 to less then 78% at I=1.5. This result is expected, since increased salt in the buffer screens the negative charges on the PAA chains, reducing electrostatic repulsion and, in turn, swelling of the networks.

Figure 18:
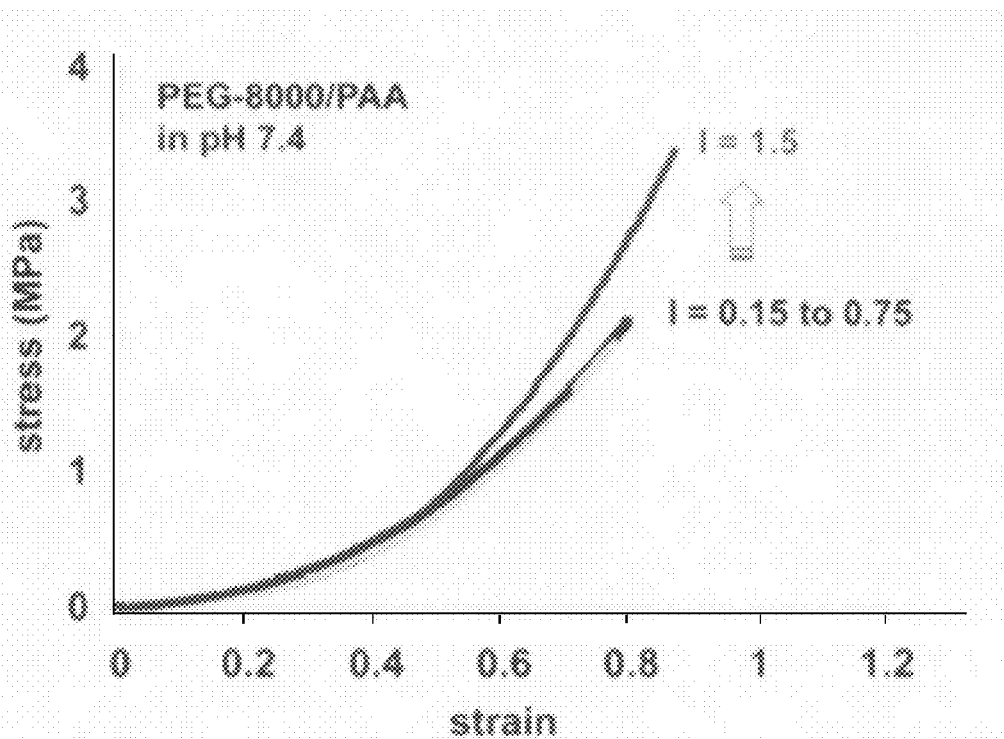
FIG. 18 shows according to an embodiment of the present invention the effect of ionic strength on the stress-strain behavior of PEG(8.0k)/PAA IPNs

Ionic strength had a modest effect on the stress-strain properties. FIG. 18 shows that stress-strain profiles of the IPNs at I=0.15 to I=0.75 were roughly equivalent. The IPN swollen in buffer with I=1.5 showed a slight enhancement in the strain hardening at higher strains. This result is consistent with the water content data, since the hydrogels with higher solids content (the IPN at higher ionic strength conditions) should have greater mechanical strength. Of note, the final modulus of the IPN in the solution with the highest ionic strength (I=1.5) appeared to be higher than those at lower ionic strength. However, the difference was small and was not found to be statistically significant.

Effect of PAA Content in Phosphate Buffered Saline

Figure 19:
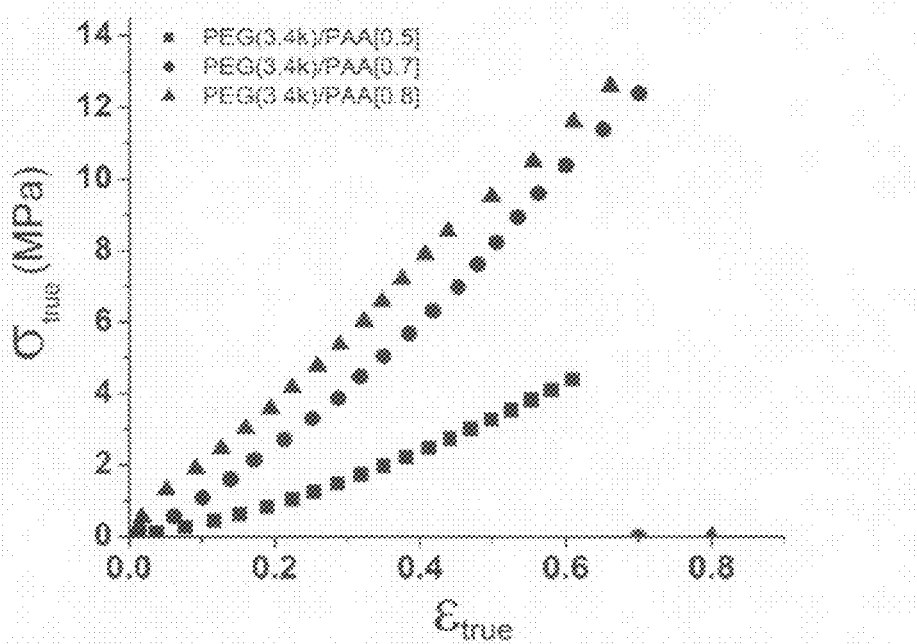
FIG. 19 shows according to an embodiment of the present invention the effect of varying the acrylic acid (AA) volume fraction in the preparation of PEG(3.4k)-based IPNs. Increasing the AA volume fraction from 0.5 (■) to 0.7 (●) and 0.8 (▲) in the IPN leads to an increase in Young's modulus.

To increase the quantity of topological interactions between the PAA and PEG networks, the polymer content of PAA was varied inside of a PEG(3.4k) first network. The volume fraction of acrylic acid in solution at the time of the second network polymerization was varied between 0.5 and 0.8 prior to polymerization. After polymerization, the IPNs were swollen to equilibrium in PBS, as was the IPN described in FIG. 15. The resultant hydrogels had different water content, from 62% in the PEG(3.4k)/PAA[0.8] IPN to 65% in the PEG(3.4k)/PAA[0.7] IPN and 77% in the PEG(3.4k)/PAA [0.5] IPN. Of note, the IPNs with increased acrylic acid concentration had lower water content, which in light of the super-absorbency of PAA is a counterintuitive result. The true stress-true strain profiles for these IPNs are shown in FIG. 19. The IPN with the highest PAA content had the highest stress-at-break and modulus, while the one with the lowest PAA content had the lowest stress-at-break and strain-at-break. Notably, the initial modulus values for these samples varied significantly, from 3.6 MPa in the PEG(3.4k)/PAA[0.5] to 12 MPa in the PEG(3.4k)/PAA[0.7] IPN and 19.6 MPa in PEG (3.4k)/PAA[0.8] IPN.

Effect of PAA Content on IPN Swelling in Pure Water

PEG(4600) single networks were prepared and imbibed with varying concentrations of AA in the second network in the presence of the photoinitiator and crosslinker. IPNs based on these AA-swollen PEG networks were then formed by UV-initiated polymerization. The IPNs were then removed from their molds, immersed in deionized water, and allowed to reach equilibrium. The volume of the IPNs relative to the PEG single networks were then measured and compared. The results are plotted in FIG. 20.

Figure 20:
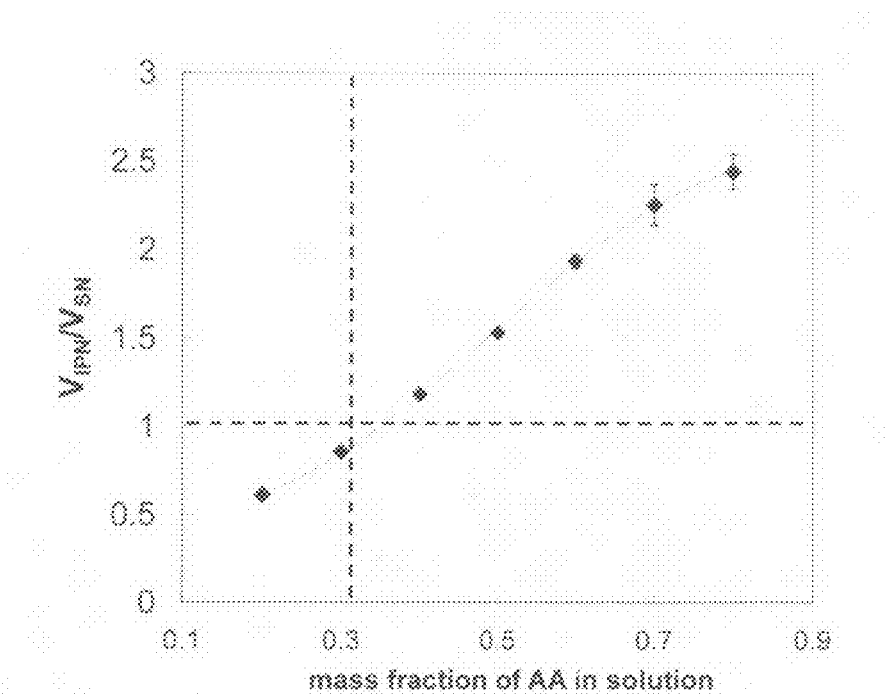
FIG. 20 shows according to an embodiment of the present invention the effect of the mass fraction of AA monomer in the second network precursor solution on the volume change in the resultant IPN. The vertical dotted line indicates the point of equimolar amounts of AA and ethylene glycol (EG) monomer units in the IPN, while the horizontal dotted line indicates where the PEG network and the PEG/PAA IPN have the same volume.

FIG. 20 shows that the volume of the IPN is increased with increased amount of AA monomer in the second network. This is consistent with the understanding that PAA absorbs water, and therefore increased PAA content in the IPN should lead to increased water absorption. Of note, however, is the fact that the IPN deswells relative to the PEG single network when the AA:EG monomer ratio is less than unity, and swells relative to the PEG network when AA is in excess to EG monomers.

Effect of PAA Content on IPN Mechanical Properties in Pure Water

Figure 21:
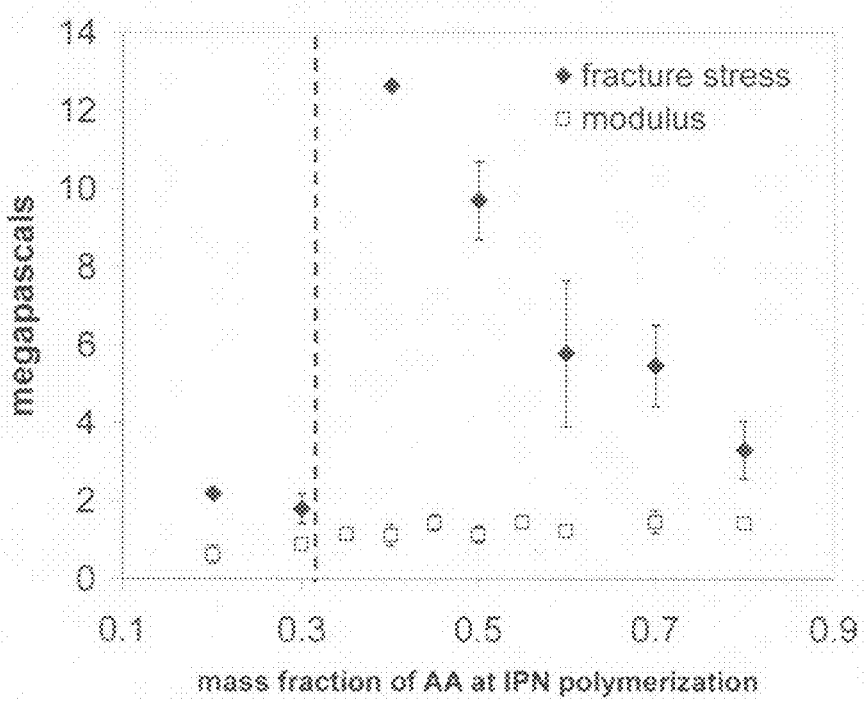
FIG. 21 shows according to an embodiment of the present invention the dependence of the fracture stress and Young's modulus of the PEG/PAA IPN on the mass fraction of AA in the IPN. The vertical dotted line indicates the point of equimolar amounts of AA and ethylene glycol (EG) monomer units in the IPN.

The same PEG/PAA IPNs of varying AA monomer content were tested by uniaxial tensile measurements. The results are shown in FIG. 21. In this figure, both the fracture stress and Young's modulus are plotted as functions of AA mass fraction at the time of polymerization. Young's modulus exhibited a modest monotonic increase as the AA concentration increased. In contrast, the fracture stress exhibited a dramatic increase in magnitude when the AA:EG ratio was increased beyond unity. As the AA monomer concentration increased, however, the fracture stress exhibited a monotonic decline.

Effect of P(AA-co-HEA) Copolymerization on IPN Mechanical Properties in Pure Water To demonstrate that an ionizable monomer is important in the second network, a series of IPNs were prepared under conditions that disrupted the degree of ionizability in the second network.

Figure 22:
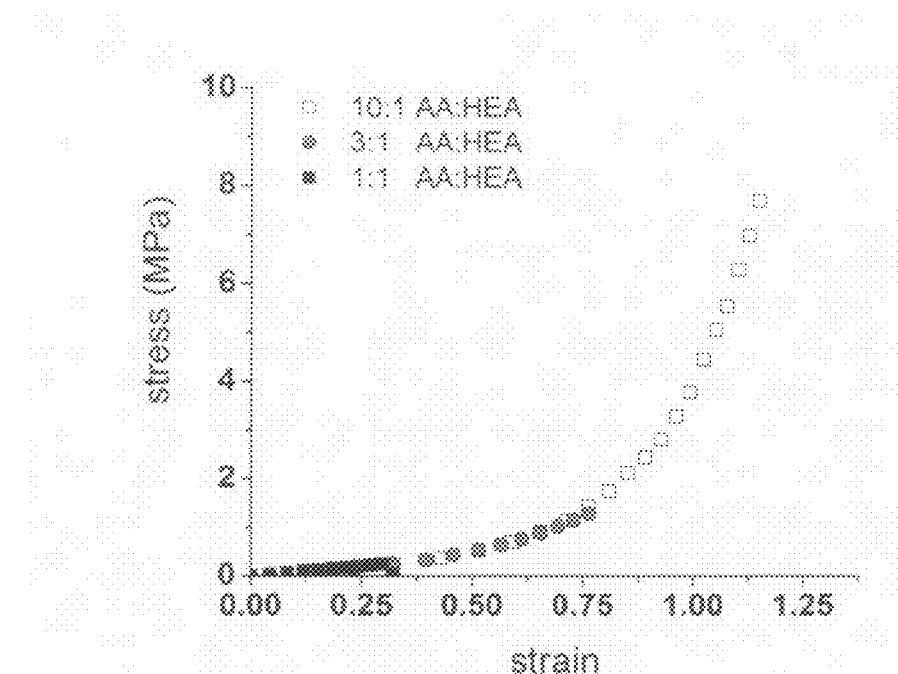
FIG. 22 shows according to an embodiment of the present invention the effect of copolymerizing HEA into the second network of PEG(8000)/PAA IPNs on stress-strain behavior.

The first method used was copolymerization of the second network with non-ionic monomers. AA monomers in the second network were mixed in three different concentrations relative to the HEA monomers: 10:1, 3:1, and 1:1. Uniaxial tensile testing experiments (FIG. 22) of the hydrogels swollen in deionized water showed that the PEG/P(AA-co-HEA) IPNs with the highest ratio of AA:HEA in the second network had significantly enhanced mechanical strength in terms of its stress-at-break and strain-at-break, while the IPNs with higher relative HEA content exhibited almost no enhancement in mechanical properties. This result demonstrates that complexation between PEG and the PAA networks (due to the presence of ionizable carboxyl acid groups in PAA donating hydrogen bonds) is necessary process step in the production of enhanced mechanical properties in these systems. Either externally applied strain or ionization of the PAA in the second leads to increased physical crosslinking between the polymeric constituents within the IPN.

Effect of AA Neutralization on IPN Mechanical Properties

Figure 23:
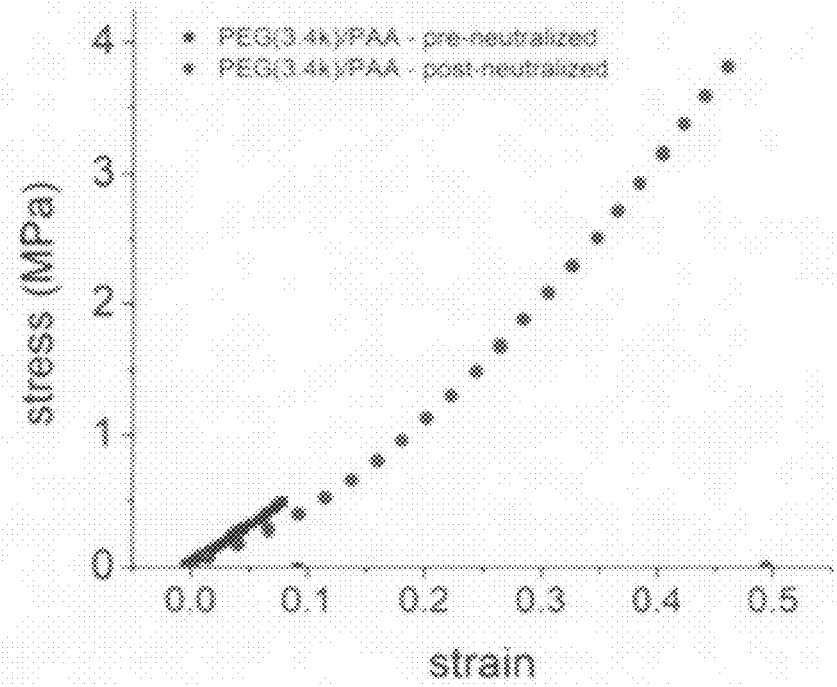
FIG. 23 shows according to an embodiment of the present invention the effect of neutralizing the AA monomer solution prior to polymerization ("pre-neutralized") on the stress-strain behavior of a PEG(3.4k)/PAA IPN (black) compared to a PEG(3.4k)/PAA IPN prepared under acidic conditions and neutralized after polymerization ("post-neutralized").
Figure 24:
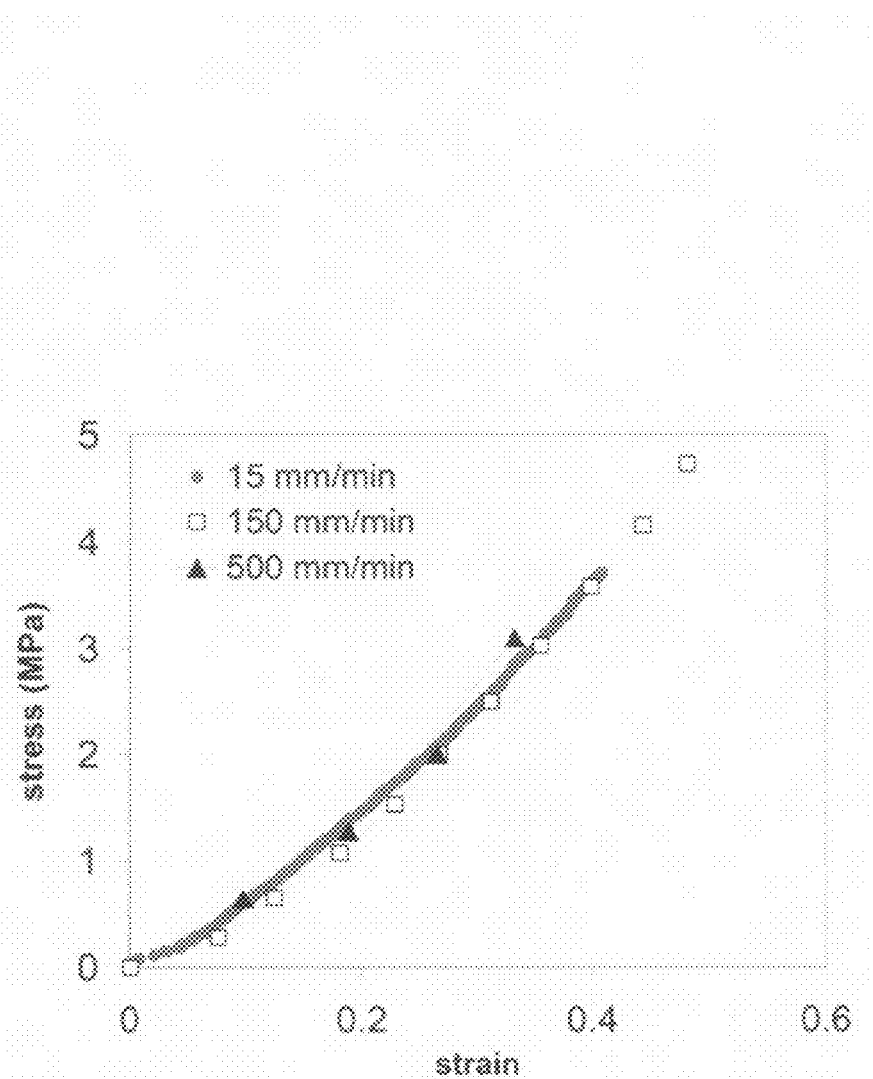
FIG. 24 shows according to an embodiment of the present invention the effect of the extension rate on the stress-strain behavior of post-neutralized PEG(3.4k)/PAA IPNs.

In this set of experiments, PEG networks were immersed in AA solutions (containing photoinitiator and crosslinker) that were partially neutralized to pH 5.5 by titration with sodium hydroxide. The monomer-swollen PEG networks were then exposed to UV light to form a partially neutralized PAA network within the PEG network. These "pre-neutralized" PEG/PAA IPNs were then washed in PBS and subjected to uniaxial tensile tests. FIG. 23 shows that neutralizing the AA solution prior to polymerization and then forming the second network leads to an IPN with the same elastic modulus, but with dramatically reduced fracture strength. The stress-at-break is reduced from nearly 4 MPa—in the case of the IPNs prepared under acidic conditions and then neutralized in PBS buffer—to roughly 0.5 MPa. This demonstrates the importance of the fabrication process in creating these strain-hardened IPNs; that is, in the preferred embodiment, ionization of the second network should be carried out after the IPN is fully formed. FIG. 24 shows that the stress-strain behavior of the strain-hardening IPN is not dependent on the extension rate of the applied uniaxial deformation.

Figure 25:
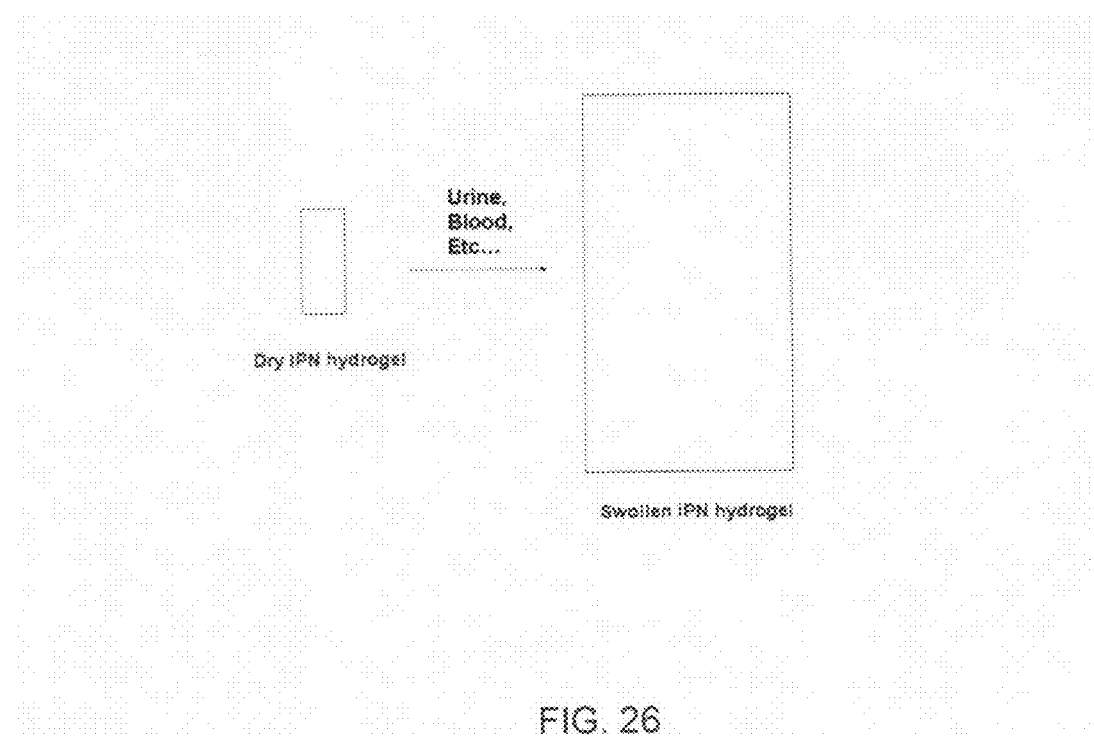
FIG. 25 shows according to an embodiment of the present invention method steps of how the IPN could function as an absorbent material for infant diapers or feminine hygiene products. Exposure of the dried hydrogel to bodily fluids such as blood or urine causes the gel to soak up the water and solutes, leading to a swollen, expanded hydrogel.

The IPNs presented in this invention swell substantially from the dry state in the presence of water or saline, and as such are useful for use as an absorbent material for diapers and feminine hygiene products. The majority of diapers produced today make use of poly(acrylic acid) polymers as the absorbent material. While these can work well, the distribution of the polymeric material is not always uniform, and can lead to leaks. A homogeneous lining or series of thin but resilient linings made from a PEG/PAA IPN may be more efficacious in uniformly absorbing and containing urine and waste matter in the diaper. Similarly, if used in combination with another paper or cotton-based absorbent material, the hydrogel can be used as a component of a tampon or pad for feminine hygiene by soaking up the aqueous part of blood. A schematic of these applications is shown in FIG. 25. Molding the gels into shapes such as cylinders or rectangular sheets is easily accomplished by casting precursor solutions in molds prior to initiating hydrogel polymerization.

Compressive Strength and Surface Friction

The mechanical properties of the IPN hydrogels of the present invention can be "tuned" to yield initial Young's modulus values (~10 MPa) that rival those of natural articular cartilage. This is a significant finding in light of the fact that hydrogels have long been thought of as potentially useful materials for the replacement of cartilage, but have suffered from a lack of mechanical strength. In fact, the most common way that hydrogels are investigated in orthopaedics is in the form of soft, often degradable scaffolds for chondrocytes to grow and eventually regenerate cartilage. A handful of cell-free, purely synthetic hydrogels are now being used in the repair of joints, but only for focal or localized regions in joints such as the knee or the vertebrae (e.g. nucleus pulposus). This is because the mechanical properties and surface characteristics of most hydrogels preclude their use in more than a small area on the joint interface. For a hydrogel to completely and functionally replace natural cartilage, it should (almost exactly) match the complex biomechanical properties of natural cartilage. In doing so, it would restore the physiologic distribution of loads to the adjacent bone, which is known to be extremely sensitive to its stress environment.

The section discussed the characterization of the PEG/PAA hydrogels in the context of the already well-known properties of articular cartilage as a prerequisite to its application as a joint surface restoration material. Experimental data are presented on the biomechanical properties of these materials that enable this material to functionally restore a cartilaginous joint.

Figure 26:
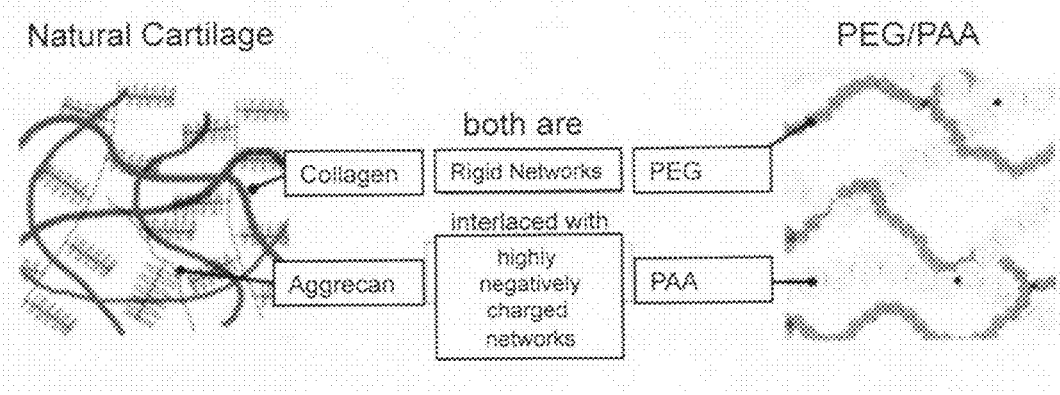
FIG. 26 shows according to an embodiment of the present invention illustrations and photos (insets) of the structures of natural cartilage (left) and PEG/PAA (right).

PEG/PAA behaves as a synthetic analog of natural cartilage. FIG. 26 juxtaposes the structures of the two materials. Natural cartilage is a highly negatively charged, water-absorbing network of glycosaminoglycans swollen within a rigid framework of collagen. Similarly, PEG/PAA is a highly negatively charged, water-absorbing polymer network of poly(acrylic acid) swollen within a rigid, neutral poly(ethylene glycol) framework. The third (and most prominent) component of both of these materials is not shown: water. The striking structural similarity between cartilage and PEG/PAA yields an equally striking functional similarity between the two materials.

Figure 27:
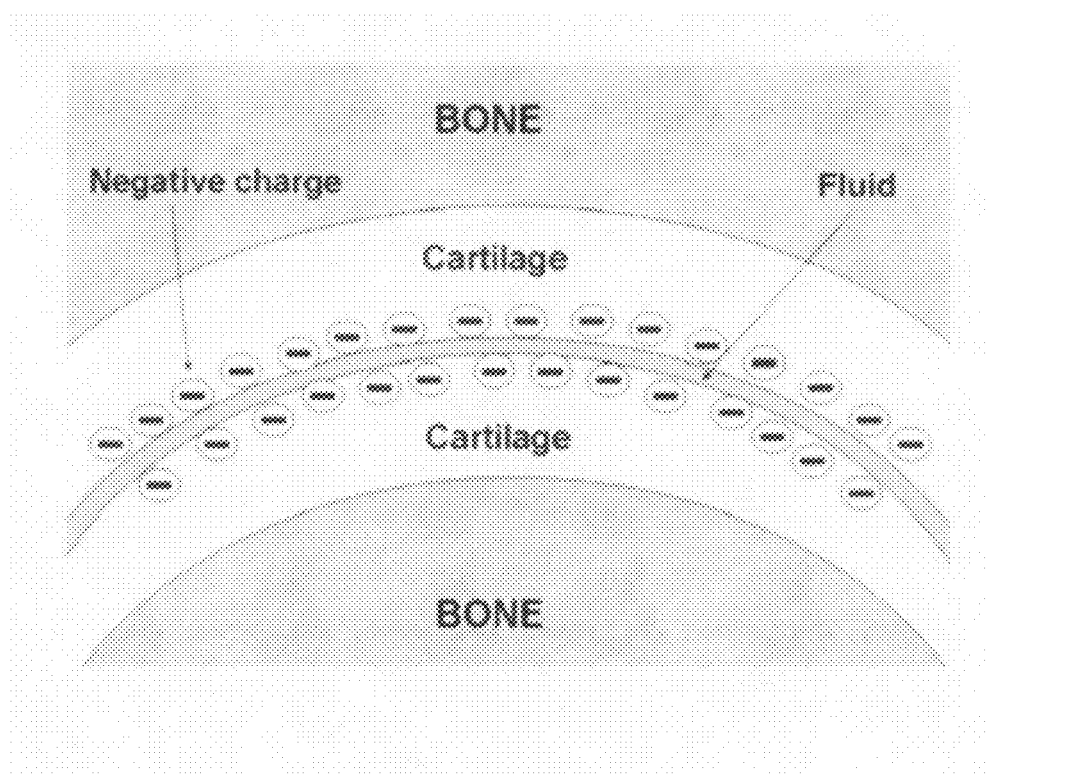
FIG. 27 shows according to an embodiment of the present invention an example showing that because PEG/PAA imitates the structure and properties of natural cartilage, it should recreate the moist lubricity of a cartilaginous joint, which is mediated by a persistent fluid film at the joint interface. The persistence of this film is made possible by movement of water out of hydrated joint tissue, the constituents of the synovial fluid, and by the abundance of negative charges.

Because PEG/PAA is a "biphasic" material like cartilage, the actual compressive loads are taken up by the fluid in the gel, thus relieving the stress on the actual solid portion of the gel. The abundance of negative charge combined with movement of this fluid in and out of cartilage results in a persistent lubricating film of fluid between cartilage surfaces in a joint. PEG/PAA, because it mimics the water content, negative charge, and elasticity of natural cartilage, has the potential to recreate a physiologic joint interface, as shown in FIG. 27.

Water Content

Figure 28:
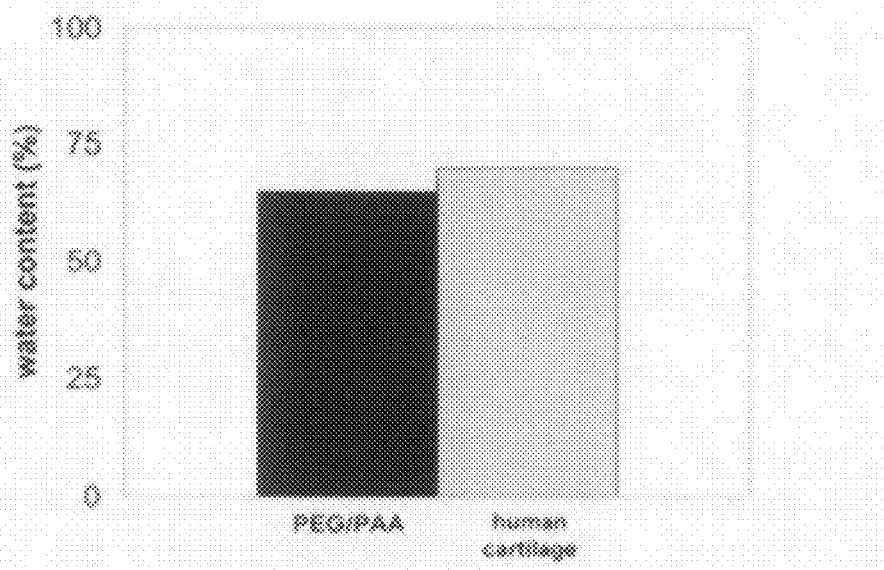
FIG. 28 shows according to an embodiment of the present invention PEG/PAA and natural cartilage contain similar amounts of water.

One of the defining characteristics of natural cartilage is that it is made up of mostly water. The water content of cartilage is critical because movement of fluid out of cartilage upon loading, in conjunction with an abundance of negatively charged functional groups, is believed to be the reason for the high lubricity observed in diarthroidal joints. A water content between 65% and 75% along with low hydraulic permeability is believed to provide a surface "weeping lubrication" mechanism that has been found in cartilage and is thought to be the reason the coefficient of friction of cartilage is very low. Therefore, the measured the equilibrium water content of PEG/PAA was compared to that of natural human cartilage, as shown in FIG. 28.

Indentation and Hydraulic Permeability

Figure 29:
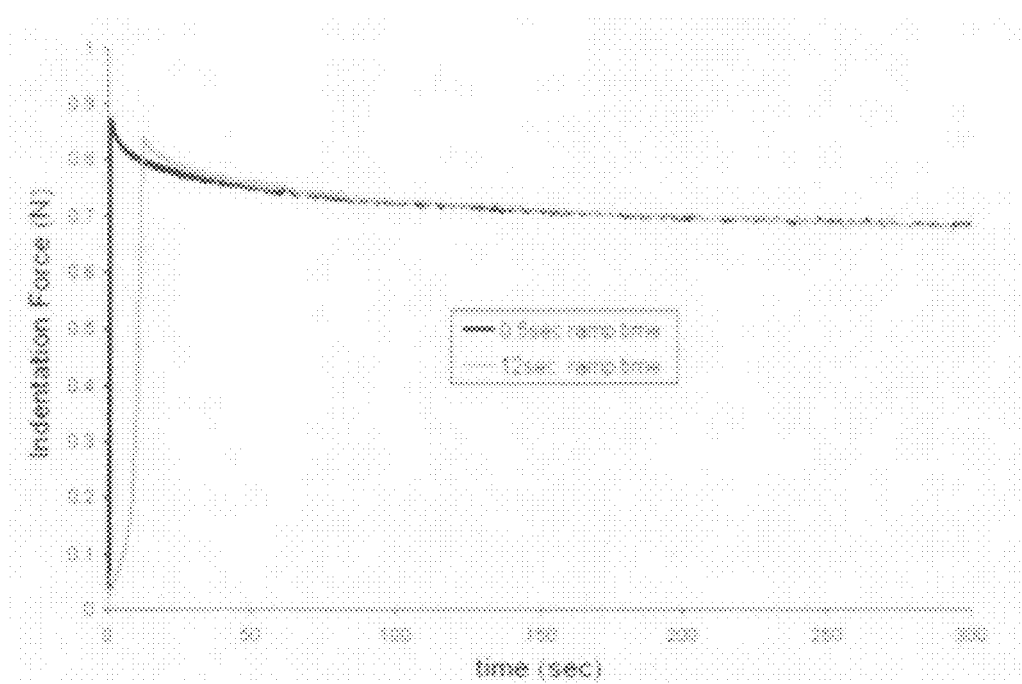
FIG. 29 shows according to an embodiment of the present invention indentation force versus time profiles for the PEG/PAA hydrogel during indentation.

Indentation experiments were carried out using a custom-made indenting apparatus. In these experiments, a constant displacement is applied and the reaction force is measured over time. The test was carried out with two different ramp times (0.5 sec and 12 sec), and the indentation force versus time data (FIG. 29) was used to extract a hydraulic permeability for the PEG/PAA hydrogel. The permeability of PEG/PAA was calculated to be $2 \times 10^{-17}$ m$^4$/N*s. This value is roughly an order of magnitude lower than those reported in the literature for natural cartilage ($1$-$50 \cdot 10^{-16}$ m$^4$/N*s).

Coefficient of Friction Measurements

In these experiments, the coefficient of friction of PEG (4.6k)/PAA fully interpenetrating networks were compared to that of ultra-high-molecular-weight polyethylene (UHMWPE, Orthoplastics, UK), a material currently used in total knee replacement and artificial disc prosthetics. These materials were also compared to a transparency sheet, which would be expected to have a higher and consistently measurable friction coefficient. The materials were placed between a sled (mass 200 g) and a glass surface cleaned and wetted with deionized water. An Instron 5844 materials tester equipped with a 10 N load cell was used to pull the sled using an Instron coefficient of friction fixture wire/pulley system that conforms to ASTM D1894 standards. The average load detected during motion of the sample was used to calculate the kinetic coefficient of friction ($\mu_k$) of the samples using the equation:

$$\mu_k = A_k/B$$

where $A_k$ is the average load reading obtained during sliding and B is the sled weight.

Figure 30:
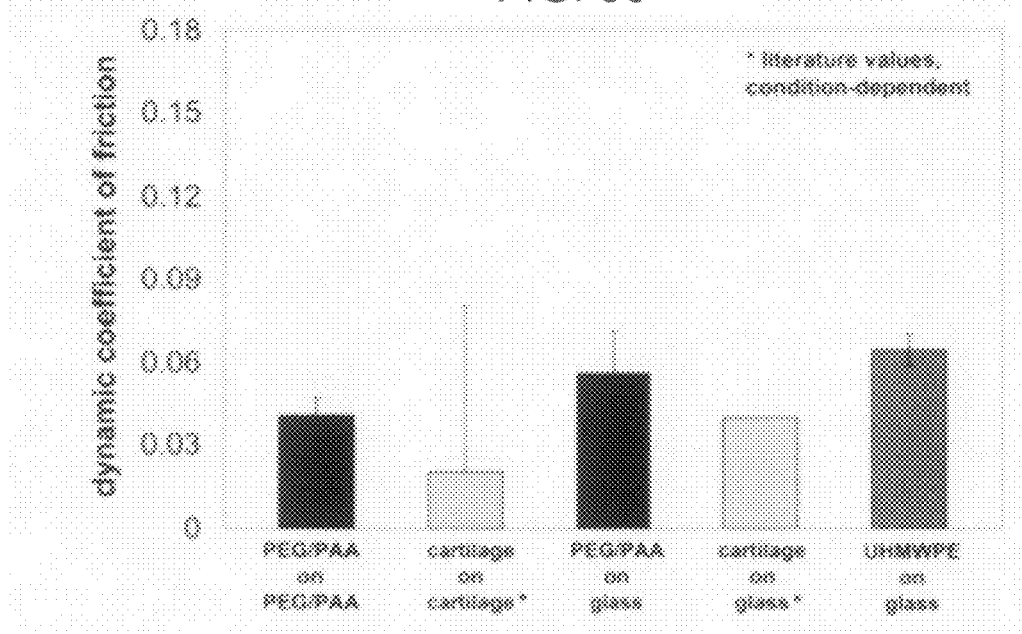
FIG. 30 shows according to an embodiment of the present invention a comparison of dynamic coefficients of friction between PEG/PAA, cartilage, and UHMWPE under various conditions.

FIG. 30 shows the mean coefficient of friction values for PEG/PAA, UHMWPE, and a transparency sheet. The coefficients of friction of PEG/PAA (3 samples) and UHMWPE (2 samples) were comparable (0.056 and 0.065, respectively), while the transparency sheet (3 samples) was much higher (0.38). The fact that the coefficient of friction of the PEG/PAA hydrogel is similar to that of the UHMWPE is favorable, especially in light of the fact that PEG/PAA is both elastic and strong when subject to compressive loads, indicating that it is a simultaneously lubricious and "cushioning" surface. In contrast, UHMWPE is lubricious but extremely rigid. The combination of lubricity and cushioning in our PEG/PAA IPNs is advantageous in joint applications, where both friction and load should be accommodated.

FIG. 30 shows data on the dynamic friction coefficient of PEG/PAA on both itself (PEG/PAA on PEG/PAA) as well as on wetted glass (PEG/PAA-on-glass). These data are juxtaposed with literature data on natural cartilage on both itself and on glass, as well as experimental data on ultra high molecular weight polyethylene (UHMWPE) on glass. The results indicate that PEG/PAA surface properties are within the range of values obtained for natural cartilage in an in vitro setting.

Tensile Measurements

Figure 31:
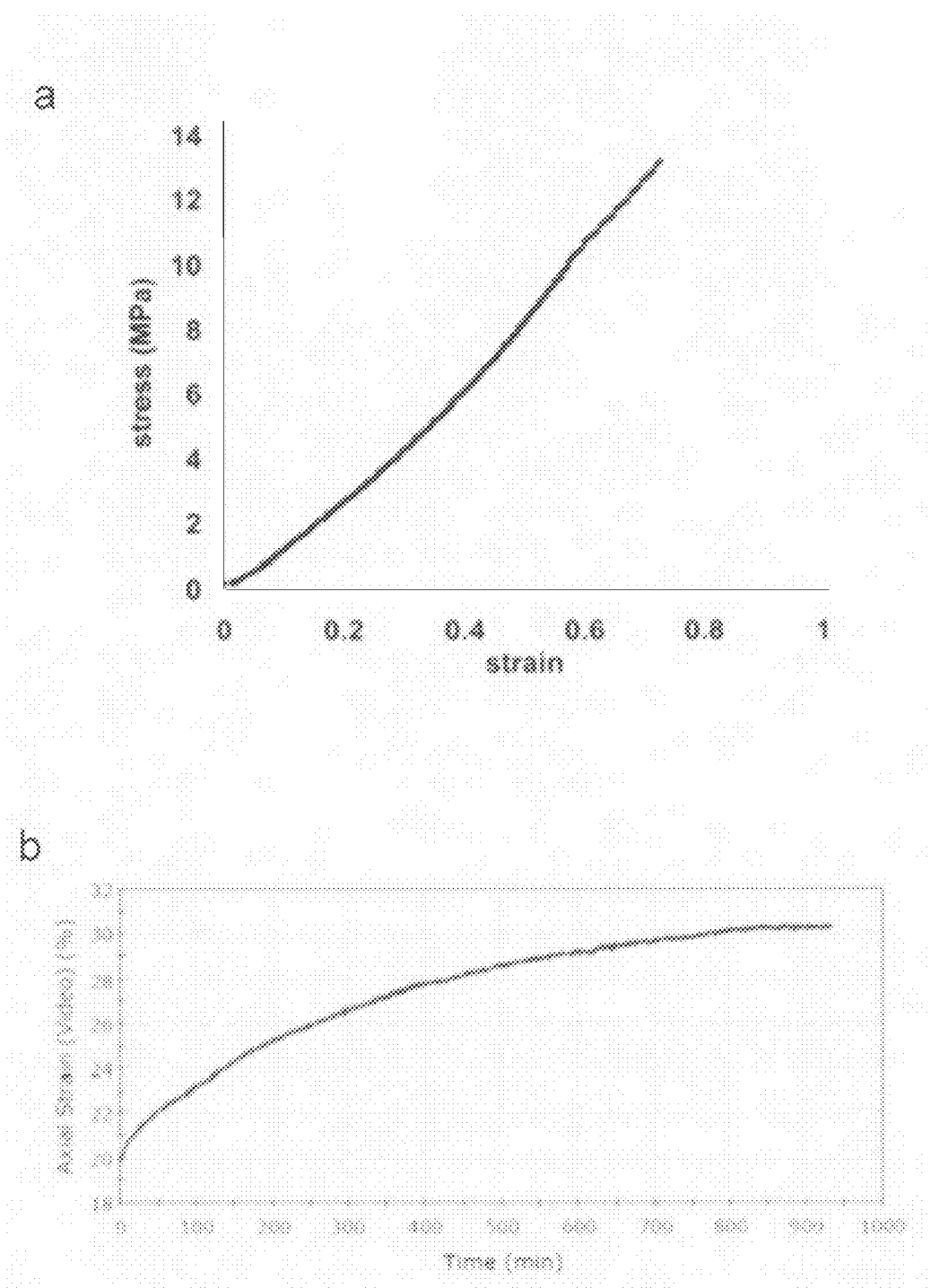
FIG. 31A. shows according to an embodiment of the present invention the true tensile stress-strain profile of a PEG/PAA hydrogel with 65% water. B. shows according to an embodiment of the present invention the tensile creep profile of a PEG/PAA hydrogel with 65% water.

One of the defining features of the strain-hardened IPN is its extremely high Young's modulus under tension—the highest modulus among hydrogels described in the scientific literature. FIG. 31a presents the stress-strain profile of a PEG/PAA IPN with a water content of 65%. Young's modulus of this material is 10 MPa, and the maximum tensile strength is also about 10 MPa, both of which are similar to the respective values of natural cartilage. Most hydrogels, including the ones being tested for orthopedic applications, have a low modulus (0.2-2.0 MPa) and are relatively fragile. FIG. 31b presents the creep behavior of the same PEG/PAA IPN (water content 65%). With an applied load of 4.5 N over 15 hours, the strain on the hydrogel increased from 20% to 30%, with equilibrium strain being achieved at about 13.3 hours.

Unconfined Compression Tests

Figure 32:
FIG. 32 shows according to an embodiment of the present invention an example showing that like cartilage, PEG/PAA is extremely strong despite being made of mostly water (65%). Shown here is an unconfined compression test in which a load of over 900 N (>200 pounds) was applied to a small cylindrical specimen (14 mm in diameter, 6.0 mm thick) without causing it to fracture.
Figure 32:
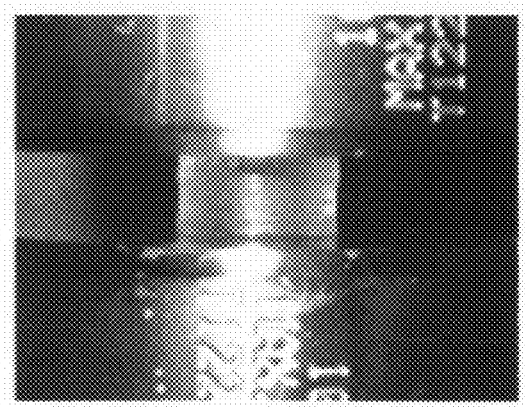
Figure 33:
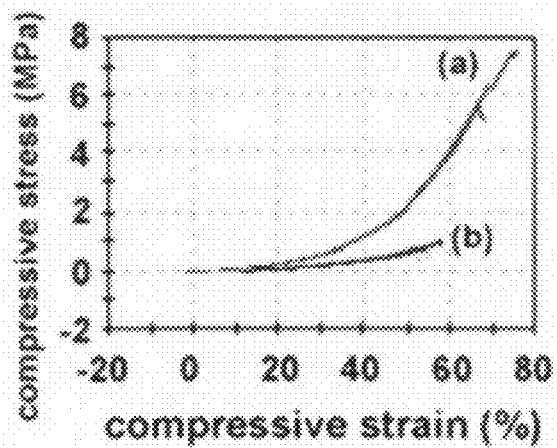
FIG. 33 shows according to an embodiment of the present invention compressive stress versus compressive strain of (a) PEG/PAA IPNs and (b) PEG single networks.
Figure 34:
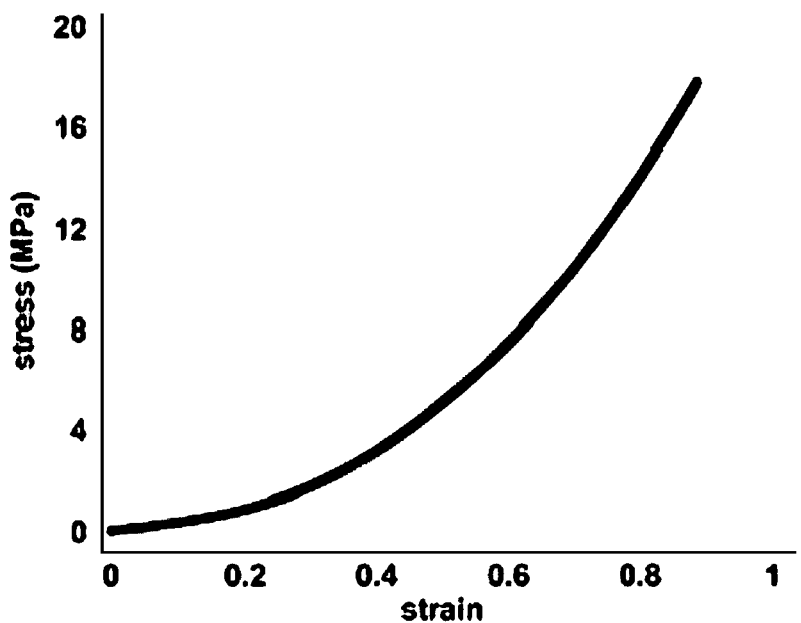
FIG. 34 shows according to an embodiment of the present invention a stress-strain profile of a PEG(3.4k)/PAA IPN under unconfined compression.

FIG. 32 shows an unconfined compression test of the IPN of the present invention. Unconfined compression tests were done (data shown in FIG. 33 and FIG. 34) to determine the material's reaction to high compressive loads. In one embodiment of the invention (FIG. 33) where a macromonomer molecular weight of 4600 Da was used in the $1^{st}$ network and 50% v/v acrylic acid was used to prepare the second network, the failure stress of the IPN in PBS (a) was near 7 MPa, while the corresponding PEG-only homopolymer in PBS (b) had a failure stress of about 1 MPa. In another embodiment (FIG. 34) where the PEG molecular weight was 3400 Da and 70% v/v acrylic acid was used to prepare the second network, the unconfined compressive strength in PBS was found to be about 18 MPa, with a failure strain under compression of over 0.8.

Confined Compression Measurements

Figure 35:
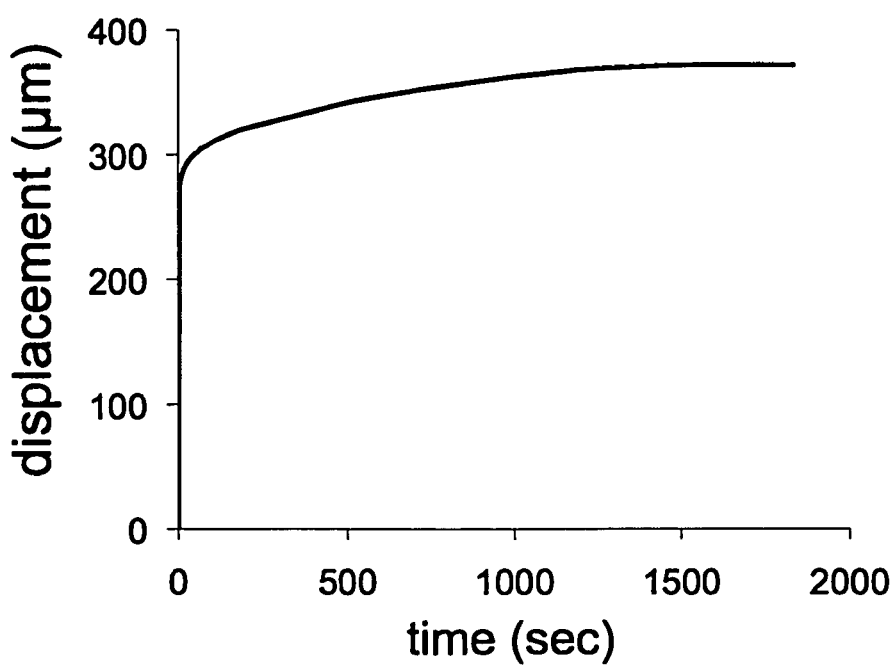
FIG. 35 shows according to an embodiment of the present invention a PEG/PAA IPN under confined compression.

Confined compression experiments were carried out on plugs of PEG/PAA confined to a cylindrical chamber, and the displacement of the material was monitored as a function of time. The indenting device was made out of sintered stainless steel and is permeable to fluids; therefore, when the sample is compressed, fluid seeping out of it can pass through the indenter. From the displacement versus time data for 7 N of load (FIG. 35), we found that the aggregate (equilibrium) modulus of the material is 2.1 MPa, which is similar to that of healthy, natural cartilage (~1.0-2.0 MPa).

Wear Measurements

Figure 36:
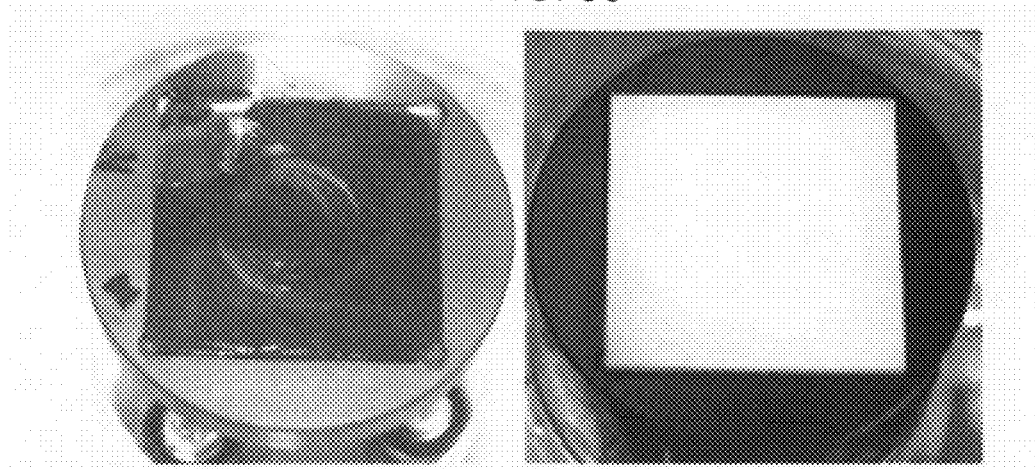
FIG. 36 shows according to an embodiment of the present invention observations of PEG/PAA (left) and UHMWPE (right) after a pin-on-disc wear test.

PEG/PAA was subjected to 250,000 cycles in a pin-on-disc wear tester following ASTM G99 specifications. A 10-mm diameter ball-tipped pin was placed onto a PEG/PAA sample under a load of 6.0 N. After first equilibrating the hydrogel sample (2 mm thick) in bovine serum for 2 hours, it was rotated at a constant velocity of 300 rpm at 37° C. in a bovine serum bath over a track radius of 10 mm. A 2.0 mm-thick piece of ultra high molecular weight polyethylene (UHMWPE, Orthoplastics, UK) was also tested under the same conditions. Neither sample showed any detectable mass loss after 250,000 cycles. Both PEG/PAA and UHMWPE had physical evidence of pin movement on their surface. The hydrogel sample actually showed a slight increase (~2%) in mass (by gravimetric measurement), possibly due to diffusion of serum proteins into the hydrogel. FIG. 36 shows the appearance of PEG/PAA and a sample of UHMWPE after the aforementioned wear test.

Figure 37:
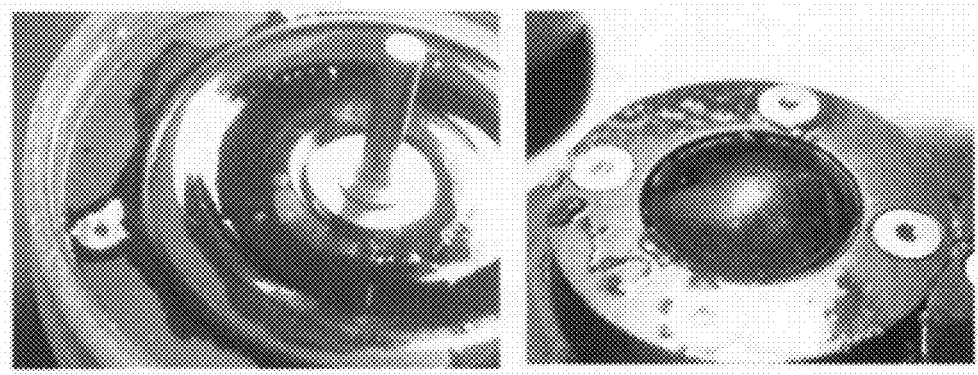
FIG. 37 shows according to an embodiment of the present invention photographs of PEG/PAA after 100,000 cycles in a custom made, hydrogel-on-hydrogel wear-tester.

PEG/PAA was then tested for 3,000,000 cycles at ~1 Hz using the custom-made tri-pin-on-disc, hydrogel-on-hydrogel tester (FIG. 37) in phosphate buffered saline. For 2 million cycles, a load of 15 pounds was applied and for the remaining 1 million cycles, a load of 25 pounds was applied. Gross observation revealed evidence of a raceway made by the hydrogel-on-hydrogel configuration. However, the concentric marks appear to have been the result of foreign body abrasion by dust or debris that entered the fluid chamber; this is supported by the fact that there were numerous additional marks with random orientations in the vicinity of the raceway. Profilometry revealed an average roughness of only 0.5 μm along the raceway, indicating that the material is highly wear-resistant in a hydrogel-on-hydrogel configuration.

Hydrogel Molding

Figure 38:
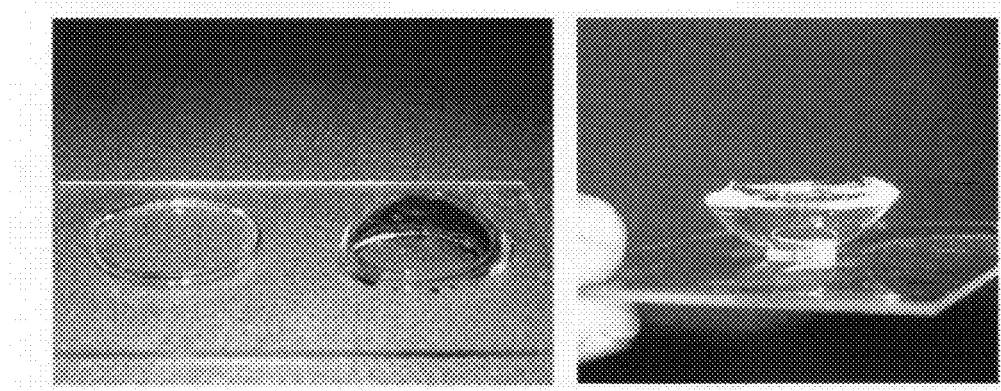
FIG. 38 shows according to an embodiment of the present invention examples of a PEG/PAA IPN molded into a hemispherical shape. The curved hydrogel was molded by photopolymerization in a curved plastic mold and then swollen to equilibrium in phosphate buffered saline (pH 7.4).

IPN hydrogels were cast within rounded molds to prove that curved geometries are achievable with this material. Photographs of these hydrogels are shown in FIG. 38.

Applications of the Strain-Hardened IPN Hydrogel

The IPN of the present invention has the advantage of attaining the following characteristics simultaneously: (1) high tensile and compressive strength, (2) low coefficient of friction on its surface, (3) high water content and swellability, (4) high permeability, (5) optical transparency, and (6) biocompatibility. For instance, it possesses the high compressive strength and lubricity necessary to serve as a replacement for articular cartilage, intervertebral discs (lumbar or cervical), bursae, menisci, and labral structures in the body. The types of orthopedic devices for which this invention is potentially useful includes total or partial replacement or resurfacing of the knee (the tibial, femoral, and/or patellar aspect), hip, shoulder, hands, fingers (e.g. carpometacarpal joint), feet, ankle, and toes. It is also useful in replacement or repair of intervertebral discs or facets. In the knee, the hydrogel can also serve as a meniscus replacement or a replacement material for the bursae in any joint such the elbow or shoulder. It also would be useful as a lining material for diapers by lending more uniform protection from leakage and a neater, more compact arrangement of absorbent matter. The material also is highly transparent, has high oxygen and glucose permeability, and is resistant to protein adsorption, making it suitable for ophthalmic lens and implant applications.

Photochemical Surface Modification

Materials according to the present invention could have biomolecules covalently linked to the IPN hydrogels. Any suitable biomolecules may be covalently linked to the IPN hydrogel. Preferably, the biomolecules are at least one of proteins, polypeptides, growth factors (e.g. epidermal growth factor) amino acids, carbohydrates, lipids, phosphate-containing moieties, hormones, neurotransmitters, or nucleic acids. any combination of small molecules or biomolecules can be used, including, but not limited to, drugs, chemicals, proteins, polypeptides, carbohydrates, proteoglycans, glycoproteins, lipids, and nucleic acids. This approach may rely, for example, on (a) photoinitiated attachment of azidobenzamido peptides or proteins, (b) photoinitiated functionalization of hydrogels with an N-hydroxysuccinimide ester, maleimide, pyridyl disulfide, imidoester, active halogen, carbodiimide, hydrazide, or other chemical functional group, followed by reaction with peptides/proteins, or (c) chemoselective reaction of aminooxy peptides with carbonyl-containing polymers. These biomolecules may, e.g., promote epithelial cell adhesion and proliferation on the nonadhesive hydrogel surface. Preferably, the heterobifunctional crosslinker used to modify the IPN hydrogel surfaces are based on azide-active-ester linkages, through molecules such as 5-azido-2-nitrobenzoyloxy-N-hydroxysuccinimide ester or its derivatives such as its sulfonated and/or its chain-extended derivatives. However, any coupling strategy can be used to create strain-hardened IPN hydrogels with bioactive surfaces. Most preferably in the case of ophthalmic applications, the biomolecules attached are at least one biomolecules found in the cornea and/or aqueous humor (e.g. collagen type I) or derivatives thereof. In addition, polymeric tethers (such as poly(ethylene glycol) chains) can be used as intervening spacer arms between polymer surfaces and biomolecules and also between biomolecules.

Transport Properties: Oxygen Permeability

IPN hydrogels composed of a PEG first network with MW 8000 and concentration of 50% w/v in $dH_2O$ in the preparation state, and a second network of polyacrylic acid with 50% v/v in $dH_2O$ in the preparation state were used to test oxygen permeability. The hydrogels were first rinsed in distilled water, then soaked in phosphate buffer solution for at least 24 hrs. The harmonic thickness of the hydrogel was then measured using Electronic thickness gauge Model ET-3 (Rehder Development company). The hydrogel was then soaked again in phosphate buffered saline solution for at least 24 hrs. Next, an electrode assembly (Rehder Development company) was attached to a polarographic cell and electrical cables were attached between the electrode assembly and a potentiostat. About 1.5 L of buffer solution was then saturated with air for at least 15 minutes and preheated to 35° C. Next, the hydrogel was carefully placed onto the electrode, the gel holder was placed over the hydrogel, and a few drops of buffer solution were placed on top of the hydrogel to keep the hydrogel saturated with buffer solution. The central part of the cell was then attached onto the cell bottom and the top part of the cell, containing the stirring rod, impeller, and coupling bushing, was attached to the top part of the cell. Air saturated buffer solution at 35° C. was then poured into the assembled cell and filled almost to the top. Next, heating coiled tubing was placed around the cell, the tubing was connected to the heating bath, insulation was wrapped around and on top of the cell, and the flow of heating fluid was turned on. The speed was then set at 400 rpm and current data was collected until the steady state was reached. The speed was then reset in 100 rpm increments up to 1200 rpm, and data was again collected. This data was then used to get the oxygen permeability by plotting the inverse of steady current versus the Reynolds number to the minus $2/3$. An oxygen permeability of 95.9±28.5 Barrers was obtained for the PEG/PAA IPN based on a PEG macromonomer with molecular weight 8000. An average oxygen permeability of 45 Barrers was obtained for the PEG/PAA IPN based on a PEG macromonomer with molecular weight 4600. For use as a contact lens material, the hydrogels according to the present invention preferably have an oxygen permeability of more than about 15 Barrers, more preferably more than 40 Barrers.

Transport Properties: Optical Clarity

The percentage (%) of light transmittance of IPN hydrogels composed of PEG with molecular weight 8000 Da (50% w/v in $dH_2O$) in the preparation state of the first network and poly(acrylic acid) (50% v/v in $dH_2O$) at 550 nm was also measured using a Varian Cary 1E/Cary 3E UV-Vis spectrophotometer following the method described by Saito et al (Saito et al, "Preparation and Properties of Transparent Cellulose Hydrogels", Journal of Applied Polymer Science, Vol. 90, 3020-3025 (2003)). The refractive index of the PEG/PAA hydrogel (with PEG MW 8000) was measured using an Abbe Refractometer (Geneq, Inc., Montreal, Quebec). The percentage of light transmittance was found to be 90%, and the refractive index was found to be 1.35.

Transport Properties: Glucose Permeability

We studied the glucose permeability across PEG/PAA IPNs, PEG polymers, of varying molecular weight, PAA polymers, and PHEMA polymers, as well as human, bovine, and pig corneas in vivo using a modified blind well chamber apparatus developed in our laboratory. In these experiments, non-porous mylar and dialysis membranes (MWCO 12 kD-14 kD) were used as negative and positive controls, respectively. Glucose diffusion coefficients for PEG/PAA were calculated using Fick's law and taking into account the sample thicknesses. Similarly, glucose diffusion coefficients for human, bovine, and pig corneas were also calculated taking into account corneal thicknesses. Our results indicate that PEG/PAA IPNs have D values between about $1.0\times10^{-06}$ cm$^2$/s and $3.0\times10^{-06}$ cm$^2$/s depending on the molecular weight of the PEG macromonomer. This is consistent with the published values of the diffusion coefficient of the human, bovine, rabbit and pig corneas we have measured in vitro, which are all on the order of $D\sim10^{-06}$ cm$^2$/sec.

We next compared PEG/PAA IPNs made with different MW PEG to single networks made of PEG or PAA. The results show that glucose permeability changes depending on the MW of PEG in the network. The threshold of permeability should be between $10^{-05}$-$10^{-07}$ cm$^2$/sec, which is the physiologic range necessary to sustain healthy corneal tissue.

As one of ordinary skill in the art will appreciate, various changes, substitutions, and alterations could be made or otherwise implemented without departing from the principles of the present invention. Accordingly, the scope of the invention should be determined by the following claims and their legal equivalents.

What is claimed is:

1. A pre-stressed interpenetrating polymer network hydrogel, comprising:
    (a) a first non-silicone network of self-linked hydrophilic non-ionic telechelic macromonomers covalently bonded to themselves and to others through their end-groups in said first network;
    (b) a second non-silicone network physically entangled with said first network wherein said second network is a network of crosslinked charged polymers formed through free radical polymerization; and
    (c) an aqueous salt solution having a neutral pH, wherein said aqueous salt solution has charged and swollen said second network in said interpenetrating polymer network hydrogel, wherein said swelling of said second network is constrained by said first network, and wherein said swelling of said second network induces an osmotic pressure within said first network resulting in said pre-stressed interpenetrating polymer network hydrogel.

2. The interpenetrating polymer network hydrogel as set forth in claim 1, wherein each of the self-linked hydrophilic non-ionic macromonomers in said first network has a molecular weight between about 275 Da to about 20,000 Da.

3. The interpenetrating polymer network hydrogel as set forth in claim 1, wherein said aqueous salt solution has a pH in the range of about 6 to 8.

4. The interpenetrating polymer network hydrogel as set forth in claim 1, wherein said first network comprises at least about 50% by dry weight telechelic macromonomers.

5. The interpenetrating polymer network hydrogel as set forth in claim 1, wherein said first network comprises hydrophilic monomers grafted onto said first network.

6. The interpenetrating polymer network hydrogel as set forth in claim 1, wherein said second network further comprises hydrophilic macromonomers grafted onto said second polymer network.

7. The interpenetrating polymer network hydrogel as set forth in claim 1, wherein said pre-stressed interpenetrating polymer network hydrogel has a tensile strength of at least about 1 MPa.

8. The interpenetrating polymer network hydrogel as set forth in claim 1, wherein said pre-stressed interpenetrating polymer network hydrogel has an initial Young's modulus of at least about 1 MPa.

9. The interpenetrating polymer network hydrogel as set forth in claim 1, wherein said pre-stressed interpenetrating polymer network hydrogel has an oxygen permeability of at least 15 Barrers.

10. The interpenetrating polymer network hydrogel as set forth in claim 1, wherein said pre-stressed interpenetrating polymer network hydrogel has an equilibrium water content of at least 50%.

11. The interpenetrating polymer network hydrogel as set forth in claim 1, wherein said pre-stressed interpenetrating polymer network hydrogel is at least about 70% transparent.

12. The interpenetrating polymer network hydrogel as set forth in claim 1, wherein the coefficient of friction of said pre-stressed interpenetrating polymer network hydrogel in an aqueous solution is less than 0.2.

13. The interpenetrating polymer network hydrogel as set forth in claim 1, further comprising biomolecules tethered to the surface of said pre-stressed interpenetrating polymer network hydrogel.

14. The interpenetrating polymer network hydrogel as set forth in claim 1, further comprising biomolecules that support cell adhesion.

15. The interpenetrating polymer network hydrogel as set forth in claim 1, wherein the degree of chemical crosslinks in said second network is less than the degree of chemical crosslinks in said first network.

* * * * *